(12) United States Patent
Chandrasekaran et al.

US010709619B2

(10) Patent No.: US 10,709,619 B2
(45) Date of Patent: *Jul. 14, 2020

(54) FASTENING TAPE AND MECHANICAL FASTENER INCLUDING MICROPOROUS FILM

(71) Applicant: 3M INNOVATIVE PROPERTIES COMPANY, St. Paul, MN (US)

(72) Inventors: Neelakandan Chandrasekaran, Woodbury, MN (US); Robert L. W. Smithson, Mahtomedi, MN (US); Timothy V. Stagg, Hudson, WI (US)

(73) Assignee: 3M Innovative Properties Company, St. Paul, MI (US)

( * ) Notice: Subject to any disclaimer, the term of this patent is extended or adjusted under 35 U.S.C. 154(b) by 486 days.

This patent is subject to a terminal disclaimer.

(21) Appl. No.: 14/897,906

(22) PCT Filed: Jun. 12, 2014

(86) PCT No.: PCT/US2014/042089
§ 371 (c)(1),
(2) Date: Dec. 11, 2015

(87) PCT Pub. No.: WO2014/201229
PCT Pub. Date: Dec. 18, 2014

(65) Prior Publication Data
US 2016/0128877 A1    May 12, 2016

Related U.S. Application Data

(60) Provisional application No. 61/977,914, filed on Apr. 10, 2014, provisional application No. 61/834,700, filed on Jun. 13, 2013.

(51) Int. Cl.
| | |
|---|---|
| *A61F 13/60* | (2006.01) |
| *A61F 13/58* | (2006.01) |
| *A61F 13/56* | (2006.01) |
| *C09J 7/29* | (2018.01) |
| *A61F 13/62* | (2006.01) |
| *A61F 13/15* | (2006.01) |
| *A61L 24/00* | (2006.01) |
| *A61L 24/04* | (2006.01) |
| *A61L 24/06* | (2006.01) |
| *A44B 18/00* | (2006.01) |
| *A61F 13/84* | (2006.01) |

(52) U.S. Cl.
CPC ............ *A61F 13/60* (2013.01); *A44B 18/008* (2013.01); *A61F 13/15756* (2013.01); *A61F 13/56* (2013.01); *A61F 13/58* (2013.01); *A61F 13/581* (2013.01); *A61F 13/622* (2013.01); *A61L 24/0036* (2013.01); *A61L 24/046* (2013.01); *A61L 24/06* (2013.01); *C09J 7/29* (2018.01); *A61F 2013/8497* (2013.01); *C09J 2201/122* (2013.01); *C09J 2201/16* (2013.01); *C09J 2201/606* (2013.01); *C09J 2205/106* (2013.01); *C09J 2407/00* (2013.01); *C09J 2421/00* (2013.01); *C09J 2427/005* (2013.01); *C09J 2433/00* (2013.01); *C09J 2475/005* (2013.01); *C09J 2483/005* (2013.01)

(58) Field of Classification Search
CPC ............ C09J 7/29; A61F 13/60; A44B 18/008
See application file for complete search history.

(56) References Cited

U.S. PATENT DOCUMENTS

| | | | |
|---|---|---|---|
| 3,930,502 A | 1/1976 | Tritsch | |
| 4,435,141 A | 3/1984 | Weisner | |
| 4,539,256 A * | 9/1985 | Shipman | B01D 67/002 156/229 |
| 4,609,584 A * | 9/1986 | Cutler | A61F 13/51401 428/156 |
| 4,775,310 A | 10/1988 | Fischer | |
| 4,839,131 A | 6/1989 | Cloeren | |
| 4,894,060 A | 1/1990 | Nestegard | |
| 4,902,553 A | 2/1990 | Hwang | |

(Continued)

FOREIGN PATENT DOCUMENTS

| | | |
|---|---|---|
| DE | 3831580 | 4/1989 |
| EP | 0341993 | 11/1989 |

(Continued)

OTHER PUBLICATIONS

US 5,389,416 A, 02/1995, Mody (withdrawn)
(Continued)

*Primary Examiner* — Victor S Chang

(57) ABSTRACT

A fastening tape, mechanical fastener, methods of making them, and personal hygiene articles including them are disclosed. The fastening tape includes a tape backing having a fastening portion, an adhesive disposed on the fastening portion, and a release surface for the adhesive. The release surface is a either a release tape attached along one of its edges to the tape backing or a release coating disposed on at least a portion of a surface of the tape backing. At least one of the tape backing or the release surface comprises a microporous film having an opaque, microporous region and at least one see-through region of lower porosity within the opaque, microporous region. The mechanical fastener includes such a microporous film and mechanical fastening elements on at least one surface. The at least one see-through region extends through the thickness of the microporous film.

20 Claims, 3 Drawing Sheets

(56) References Cited

U.S. PATENT DOCUMENTS

| | | | |
|---|---|---|---|
| 5,120,594 A | 6/1992 | Mrozinski | |
| 5,236,963 A | 8/1993 | Jacoby et al. | |
| 5,256,231 A | 10/1993 | Gorman | |
| 5,491,188 A | 2/1996 | Ikeda | |
| 5,510,161 A | 4/1996 | Lloyd | |
| 5,516,567 A | 5/1996 | Roessler et al. | |
| 5,572,291 A | 11/1996 | Moriguchi | |
| 5,845,375 A | 12/1998 | Miller | |
| 5,868,987 A | 2/1999 | Kampfer | |
| 5,897,541 A | 4/1999 | Uitenbroek | |
| 5,953,797 A | 9/1999 | Provost | |
| 6,075,179 A | 6/2000 | McCormack | |
| 6,110,588 A | 8/2000 | Perez | |
| 6,132,660 A | 10/2000 | Kampfer | |
| 6,190,594 B1 | 2/2001 | Gorman | |
| 6,190,758 B1 | 2/2001 | Stopper | |
| 6,287,665 B1 | 9/2001 | Hammer | |
| 6,334,504 B1 | 1/2002 | Sato | |
| 6,368,097 B1 | 4/2002 | Miller | |
| 6,368,742 B2 | 4/2002 | Fisher | |
| 6,420,024 B1 | 7/2002 | Perez | |
| 6,544,633 B1 | 4/2003 | Ogura | |
| 6,586,073 B2 | 7/2003 | Perez | |
| 6,627,133 B1 | 9/2003 | Tuma | |
| 6,632,850 B2 | 10/2003 | Hughes | |
| 6,669,887 B2 | 12/2003 | Hilston | |
| 6,708,378 B2 | 3/2004 | Parellada | |
| 6,719,742 B1 | 4/2004 | McCormack | |
| 6,815,048 B2 | 11/2004 | Davidson | |
| 6,861,132 B2 | 3/2005 | Ikeda et al. | |
| 7,168,139 B2 | 1/2007 | Seth | |
| 7,198,743 B2 | 4/2007 | Tuma | |
| 7,214,334 B2 | 5/2007 | Jens | |
| 7,220,478 B2 | 5/2007 | McCormack | |
| 7,423,088 B2 | 9/2008 | Mäder | |
| 7,682,689 B2 | 3/2010 | Sadamitsu et al. | |
| 7,897,078 B2 | 3/2011 | Petersen | |
| 8,324,444 B2 | 12/2012 | Hansson | |
| 8,613,736 B2 | 12/2013 | Schnabel | |
| 8,680,169 B2 | 3/2014 | Yamada | |
| 9,278,471 B2 | 3/2016 | Chandrasekaran | |
| 9,358,714 B2 * | 6/2016 | Chandrasekaran | B32B 3/30 |
| 10,076,450 B2 * | 9/2018 | Chandrasekaran | B32B 3/30 |
| 2002/0062117 A1 | 5/2002 | Raufman | |
| 2003/0035943 A1 | 2/2003 | Jones | |
| 2003/0091617 A1 | 5/2003 | Mrozinski | |
| 2003/0091618 A1 | 5/2003 | Seth | |
| 2003/0148091 A1 | 8/2003 | Ikeda et al. | |
| 2003/0207137 A1 | 11/2003 | Kong et al. | |
| 2004/0209063 A1 | 10/2004 | Gallagher et al. | |
| 2005/0215963 A1 | 9/2005 | Autran et al. | |
| 2005/0288510 A1 | 12/2005 | Mader et al. | |
| 2006/0177632 A1 | 8/2006 | Jacoby | |
| 2007/0020448 A1 | 1/2007 | Hubbard | |
| 2007/0082154 A1 | 4/2007 | Ambroise | |
| 2007/0100306 A1 | 5/2007 | DiZio et al. | |
| 2007/0286976 A1 | 12/2007 | Selen | |
| 2008/0000581 A1 | 1/2008 | Nison | |
| 2008/0000793 A1 | 1/2008 | Lambertus | |
| 2008/0044617 A1 * | 2/2008 | Schmitz | B29C 51/165 428/71 |
| 2008/0233373 A1 | 9/2008 | Coburn | |
| 2009/0258212 A1 | 10/2009 | Jacoby | |
| 2009/0258560 A1 | 10/2009 | Kristiansen | |
| 2010/0010168 A1 | 1/2010 | Wolfschwenger et al. | |
| 2010/0301510 A1 | 12/2010 | Coburn | |
| 2011/0088828 A1 | 4/2011 | Misek | |
| 2011/0147475 A1 | 6/2011 | Biegler | |
| 2011/0151171 A1 | 6/2011 | Biegler | |
| 2011/0264064 A1 | 10/2011 | Arora | |
| 2012/0220973 A1 | 8/2012 | Chan | |
| 2012/0242009 A1 | 9/2012 | Mullane | |
| 2012/0308755 A1 | 12/2012 | Gorman | |
| 2012/0329647 A1 | 12/2012 | Nellenbach | |
| 2013/0202828 A1 | 8/2013 | Jacoby | |
| 2014/0044934 A1 | 2/2014 | Bills | |
| 2014/0093716 A1 | 4/2014 | Hanschen | |
| 2016/0278987 A1 | 9/2016 | Chandrasekaran | |

FOREIGN PATENT DOCUMENTS

| | | | |
|---|---|---|---|
| EP | 0539504 | | 5/1993 |
| EP | 0581323 | | 2/1994 |
| EP | 0925769 | | 6/1999 |
| EP | 0974326 | | 2/2000 |
| EP | 1816158 | | 8/2007 |
| GB | 2252838 | | 8/1992 |
| GB | 2252839 | | 8/1992 |
| GB | 2323325 | | 9/1998 |
| GB | 2323327 | | 9/1998 |
| JP | 06033022 A | * | 2/1994 |
| JP | 10114357 A | * | 5/1998 |
| JP | 2000169608 | | 6/2000 |
| JP | 3414494 | | 6/2003 |
| JP | 2004331944 | | 11/2004 |
| JP | 2005-279005 | | 10/2005 |
| JP | 2006-314361 | | 11/2006 |
| WO | WO 1994-06387 | | 3/1994 |
| WO | WO 9605262 | | 2/1996 |
| WO | WO 2002-081557 | | 10/2002 |
| WO | WO 2004-075803 | | 9/2003 |
| WO | WO 2006-023442 | | 3/2006 |
| WO | WO 2006-073919 | | 7/2006 |
| WO | WO 2007-032965 | | 3/2007 |
| WO | WO 2009-040767 | | 4/2009 |
| WO | WO 2010-065602 | | 6/2010 |
| WO | WO 2011-119323 | | 9/2011 |
| WO | WO 2013-152287 | | 10/2013 |
| WO | WO 2014-201219 | | 12/2014 |
| WO | WO 2014-201221 | | 12/2014 |

OTHER PUBLICATIONS

Abstract of JP06033022. See above fr date and inventor.*
Translation of JP06033022. See above for date and inventor.*
Abstract of JP10114357. See above for date and inventor.*
Chu, "Crystal transformation and micropore formation during uniaxial drawing of β-form polypropylene film", *Polymer*, 1995, vol. 36, No. 13, pp. 2523-2530.
Chu, "Microvoid formation process during the plastic deformation of β-form polypropylene", *Polymer*, 1994, vol. 35, No. 16, pp. 3442-3448.
Jones, "Crystalline forms of isotactic polypropylene", 1964, vol. 75, No. 1, pp. 134-158.
International Search report for PCT International Application No. PCT/US2014/042089 dated Sep. 22, 2014, 3 pages.

* cited by examiner

FASTENING TAPE AND MECHANICAL FASTENER INCLUDING MICROPOROUS FILM

CROSS-REFERENCE TO RELATED APPLICATION

This application is a national stage filing under 35 U.S.C. 371 of PCT/US2014/042089 filed Jun. 12, 2014, which claims priority to U.S. Application Nos. 61/834,700, filed Jun. 13, 2013, and 61/977,914, filed Apr. 10, 2014, the disclosures of which are incorporated by reference in their entirety herein.

BACKGROUND

A variety of different personal hygiene articles (e.g., absorbent articles such as diapers, adult incontinence products, and sanitary napkins) that include different printed and/or colored regions are available in the market. Printing or coloring on such articles can be attractive to the consumer and help the consumer differentiate between different brands. Some manufacturers of absorbent articles print with multi-colored graphics that are a signature of their brand. Others may use monochromatic printing on the articles. Printing approaches to providing a differentiated product generally use ink, colored adhesives, or heat- or pressure-activated chemical colorants, each of which adds cost to the product that is passed on to consumers. Some recent examples of absorbent articles with patterns or colors include those described in U.S. Pat. No. 8,324,444 (Hansson et al.) and U.S. Pat. Appl. Pub. Nos. 2011/0264064 (Arora et al.) and 2012/0242009 (Mullane et al.).

SUMMARY

The present disclosure provides a fastening tape and mechanical fastener, which may be a component of a fastening tape. The fastening tape and the mechanical fastener each include a microporous film. The microporous film has an opaque, microporous region and at least one see-through region of lower porosity within the opaque, microporous region. The see-through region of lower porosity has a predetermined (in other words, designed) shape. Advantageously, the see-through region can be in the form of a wide variety of patterns, numbers, pictures, symbols, alphabetical letters, bar codes, or combinations thereof that can be selected to be aesthetically pleasing to a user. The see-through region can also be in the form of a company name, brand name, or logo that may be readily identified by a customer. The fastening tape or mechanical fastener according to the present disclosure can be readily customized depending on the requirements of a particular product. The see-through region provides a visual image without the use of inks or other expensive, color-providing chemicals.

In one aspect, the present disclosure provides a fastening tape. The fastening tape includes a tape backing comprising a fastening portion, an adhesive disposed on the fastening portion, and a release surface for the adhesive. The release surface is a either a release tape attached along one of its edges to the tape backing or a release coating disposed on at least a portion of a surface of the tape backing. At least one of the tape backing or the release surface comprises a microporous film having an opaque, microporous region and at least one see-through region of lower porosity within the opaque, microporous region. When the release surface is a release coating disposed on at least a portion of a surface of the tape backing, both the tape backing and the release surface can simultaneously comprise the microporous film having the opaque, microporous region and the at least one see-through region of lower porosity within the opaque, microporous region. The fastening tape may be a disposal tape.

The fastening portion is typically on a first end of the fastening tape, and the opposite, second end typically can attach the fastening tape to a personal hygiene article. Accordingly, in another aspect, the present disclosure provides a personal hygiene article. The personal hygiene article includes a chassis with a topsheet, a backsheet, an absorbent component between the topsheet and the backsheet, first and second opposing longitudinal edges extending from a rear waist region to an opposing front waist region, and a fastening tab attached to the first longitudinal edge of the chassis in the rear waist region or the front waist region. The fastening tab includes a microporous film having an opaque, microporous region and at least one see-through region of lower porosity within the opaque, microporous region. The microporous film can form at least a portion of a tape backing, release tape, or mechanical fastener on the fastening tab. The personal hygiene article can also be a pants style personal hygiene article including a chassis with a topsheet, a backsheet, an absorbent component between the topsheet and the backsheet, and the fastening tab attached to at least a portion of the backsheet. The fastening tape in this embodiment may be a disposal tape.

In another aspect, the present disclosure provides a mechanical fastener. The mechanical fastener includes a microporous film having a thickness, an opaque, microporous region, and at least one see-through region of lower porosity within the opaque, microporous region. The at least one see-through region extends through the thickness of the microporous film. Mechanical fastening elements are on at least one surface of the mechanical fastener. The mechanical fastener may include male or female fastening elements; in other words, it may comprise hooks or loops.

In another aspect, the present disclosure provides a method of making a mechanical fastener. The method includes providing a mechanical fastener comprising mechanical fastening elements on at least one surface of a microporous film and collapsing some pores in the microporous film to form at least one see-through region of lower porosity within an opaque, microporous region of the microporous film. In some embodiments, providing the mechanical fastener includes forming upstanding posts on a film comprising at least one of a beta-nucleating agent, a filler, or a diluent and stretching the film to provide the microporous film. In some embodiments, providing the mechanical fastener includes laminating a fibrous loop web to a film comprising at least one of a beta-nucleating agent, a filler, or a diluent and stretching the film to provide the microporous film.

In another aspect, the present disclosure provides a method of making a fastening tape. The method includes providing a microporous film, collapsing some pores in the microporous film to form at least one see-through region of lower porosity within an opaque, microporous region of the microporous film, assembling at least a portion of the microporous film including the at least one see-through region of lower porosity and the opaque, microporous region into the fastening tape, and coating an adhesive on a fastening portion of the fastening tape. The fastening tape has a tape backing with the fastening portion and a release surface. The release surface is a release tape attached along one of its edges to the tape backing or a release coating disposed on at least a portion of a surface of the tape backing. At least one of the tape backing or the release surface includes the microporous film having the opaque, microporous region and the at least one see-through region of lower porosity within the opaque, microporous region.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure in their relative sense only. It will be understood that, unless otherwise noted, those terms are used merely as a matter of convenience in the description of one or more of the embodiments.

The term "microporous" refers to having multiple pores that have an average dimension (in some cases, diameter) of up to 10 micrometers. At least some of the multiple pores should have a dimension on the order of or larger than the wavelength of visible light. For example, at least some of the pores should have a dimension (in some cases, diameter) of at least 400 nanometers. Pore size is measured by measuring bubble point according to ASTM F-316-80. The pores may be open cell pores or closed cell pores. In some embodiments, the pores are closed cell pores.

The term "see-through" refers to either transparent (that is, allowing passage of light and permitting a clear view of objects beyond) or translucent (that is, allowing passage of light and not permitting a clear view of objects beyond). The see-through region may be colored or colorless. It should be understood that a "see-through" region is large enough to be seen by the naked eye.

The term "within" with regard to the at least one see-through region with the opaque, microporous region means that the opaque, microporous region may border the at least one see-through region on at least two sides or more. In some embodiments, the opaque, microporous region surrounds the at least one see-through region. Generally, the at least one see-through region is not found only at the edge of the microporous film.

The thickness of a film should be understood to be its smallest dimension. It is generally referred to as the "z" dimension and refers to the distance between the major surfaces of the film.

The term "upstanding" with regard to the mechanical fastening elements refers to posts that protrude from the thermoplastic backing and includes posts that stand perpendicular to the backing and posts that are at an angle to the backing other than 90 degrees.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
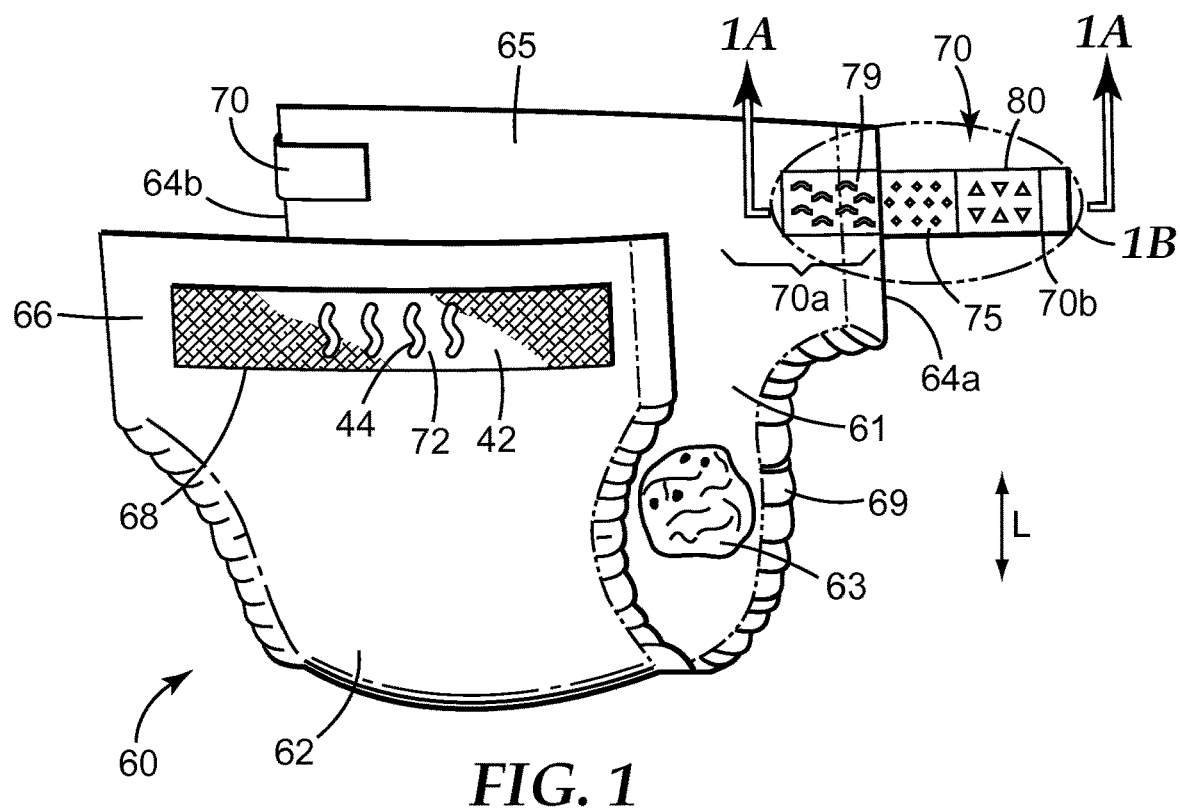
FIG. 1 is a perspective view of an embodiment of a personal hygiene article incorporating a fastening tape and/or mechanical fastener according to the present disclosure.

FIG. 1 is a perspective view of an embodiment of a personal hygiene article incorporating a fastening tape and/or mechanical fastener according to the present disclosure. The personal hygiene article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 70 arranged at the two longitudinal edges 64a, 64b of diaper 60. The diaper 60 may comprise an elastic material 69 along at least a portion of longitudinal edges 64a and 64b to provide leg cuffs. When attaching the diaper 60 to a wearer's body, the user's ends 70b of fastening tabs 70 can be attached to a target area 68 comprising fibrous material 72 arranged on the backsheet 62 of the front waist region 66. The longitudinal direction "L" of the personal hygiene article (e.g., diaper 60) refers to the direction that the article extends from the front to rear of the user. Therefore, the longitudinal direction refers to the length of the personal hygiene article between the rear waist region 65 and the front waist region 66. The lateral direction of the personal hygiene article (e.g., diaper 60) refers to the direction that the article extends from the left side to the right side (or vice versa) of the user (i.e., from longitudinal edge 64a to longitudinal edge 64b in the embodiment of FIG. 1).

Figure 1A:
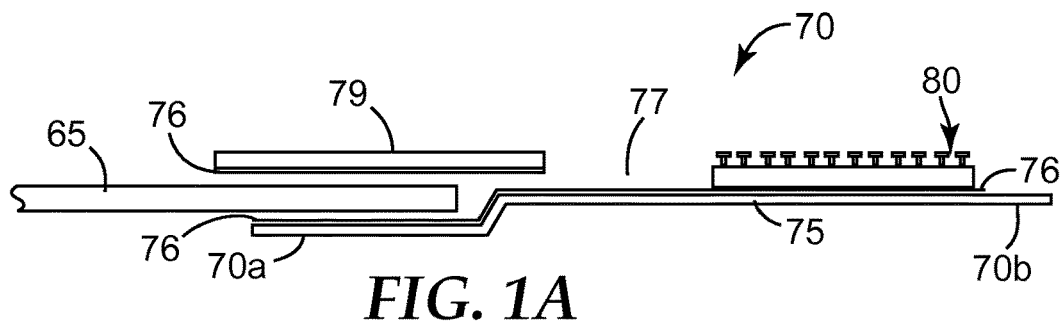
FIG. 1A is an embodiment of an exploded cross-sectional side view taken along line 1A-1A of FIG. 1.

An exemplary cross-section of the fastening tab 70 taken through line 1A-1A in FIG. 1 is shown in FIG. 1A. Fastening tab 70 has a manufacturer's end 70a secured to the diaper rear waist region 65 and a user's end 70b that includes the fastening portion. The manufacturer's end 70a corresponds to the part of fastening tab 70 which is fixed or secured to the diaper 60 during the manufacture of the diaper 60. The user's end is typically gripped by the user when attaching the diaper 60 to the wearer and is typically not fixed to the diaper during manufacturing. Fastening tab 70 usually extends beyond longitudinal edges 64a, 64b of the diaper 60.

In the embodiment illustrated in FIG. 1A, fastening tab 70 comprises a tape backing 75 bearing adhesive 76. Adhesive 76 joins optional mechanical fastener 80 to the tape backing 75 and joins the tape backing 75 to the rear waist region 65 of the diaper. In the illustrated embodiment, exposed adhesive 77 may be present between the mechanical fastener 80 and the diaper rear waist region 65. Fastening tab 70 further comprises release tape 79 to contact the exposed part of adhesive 77 when the user's end 70b is folded onto diaper rear waist region 65 (e.g., during packaging and shipping of diaper 60 as shown for the fastening tab 70 at longitudinal edge 64b). As shown in FIG. 1A, the release tape 79 is attached to the tape backing 75 (in some embodiments, directly attached as shown) along only one of its edges, leaving the opposite edge to be joined to the diaper rear waist region 65 during the manufacture of the personal hygiene article. The release tape 79 therefore is generally understood in the art to be permanently attached to the fastening tab 70 and ultimately to the personal hygiene article. In this way, release tape 79 is understood to be different from a release liner that is temporarily placed over exposed adhesive and discarded when the adhesive is in use. The release tape 79 may be joined to the tape backing 75 and diaper rear waist region 65 using adhesive 76 although in some embodiments, thermobonding, ultrasonic bonding, or laser bonding may be useful. Other configurations of release tape 79 are possible depending on the configuration of the attachment of the fastening tab 70 to diaper 60. The tape backing 75 at the user's end 70b of the fastening tab 70 may exceed the extension of the adhesive 76 and optional mechanical fastener 80 thereby providing a fingerlift.

In some embodiments, when the fastening tape according to the present disclosure is manufactured, the release tape 79 is folded back on itself and can be applied to the tape backing 75 in a pre-folded condition although it is possible in some cases to fold the release tape 79 after attaching one end to the tape backing. The release tape 79 may also be attached to the tape backing 75 using a separate strip or patch (not shown). The strip or patch can be made from a material such as any of the films and fibrous materials described herein below. When the release tape 79 is coated with an adhesive layer on a surface opposite the release surface, the strip or patch can adhere to both the release tape 79 and the tape backing 75 to connect them. Otherwise, other bonding methods (e.g., ultrasonic bonding) may be used.

FIG. 1 illustrates a variety of embodiments of the fastening tape and mechanical fastener 80 according to the present disclosure in the same diaper 60. As illustrated in FIG. 1 and the expanded view of the fastening tab 70 shown in FIG. 1B, release tape 79 is a microporous film having an opaque, microporous region 12 and at least one see-through region of lower porosity 14 within the opaque, microporous region 12. Also, in the illustrated embodiment, tape backing 75 is a microporous film having an opaque, microporous region 22 and at least one see-through region of lower porosity 24 within the opaque, microporous region 22. Furthermore, mechanical fastener 80 comprises a microporous film having an opaque, microporous region 32 and at least one see-through region of lower porosity 34 within the opaque, microporous region 32. Finally, target area 68 includes a mechanical fastener comprising a microporous film having an opaque, microporous region 42 and at least one see-through region of lower porosity 44 within the opaque, microporous region 42. Although fastening tab 70 includes release tape 79, tape backing 75, and mechanical fastener 80 all including a microporous film having an opaque, microporous region and at least one see-through region of lower porosity within the opaque, microporous region, any one of these or any combination of two of these may be present in the fastening tab according to the present disclosure. As both target area 68 and mechanical fastener 80 can include at least one see-through region of lower porosity 34, 44 within the opaque, microporous region 32, 42, it should be understood that both hook and loop materials are included in the mechanical fasteners according to the present disclosure.

Figure 1B:
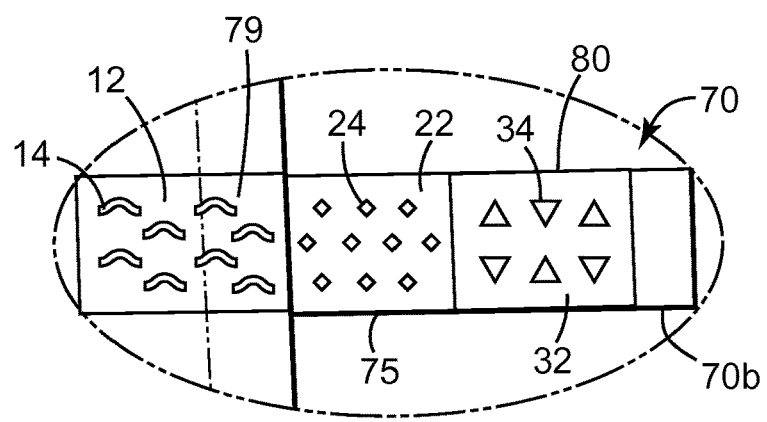
FIG. 1B is an expanded view of the indicated area of FIG. 1.

In FIGS. 1 and 1B, each of the release tape 79, tape backing 75, and mechanical fasteners 80 and 72 include a see-through region of lower porosity 14, 24, 34, and 44 that is included in a pattern of see-through regions of lower porosity although this is not a requirement. There may be more than one see-through region of lower porosity within the opaque, microporous region that does not necessarily form a repeating pattern. For example, multiple see-through regions in the form of alphabetical letters can be used together to form a word. The see-through region(s) of lower porosity 14, 24, 34, and 44 or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

In the fastening tape and mechanical fastener according to the present disclosure, the relative areas of the at least one see-through region of lower porosity and the opaque, microporous region may be different in different embodiments. The at least one see-through region of lower porosity can make up at least 5, 10, 20, 25, 50, 75, or 90 percent of the visible area of the tape backing, release tape, or mechanical fastener. For some patterns (e.g., a pattern of rhombuses or other geometric shapes), the opaque microporous region may appear as strands separating the see-through regions. For other patterns, the see-through regions may appear more widely separated on a continuous, opaque, microporous background.

The size of any individual see-through area of lower porosity in the fastening tape and mechanical fastener according to the present disclosure may be at least 0.3 mm$^2$, 0.4 mm$^2$, 0.5 mm$^2$, or 0.7 mm$^2$. Generally, if the color contrast between the opaque, microporous region and any underlying layer beneath the any individual see-through area of lower porosity is relatively large, smaller individual see-through areas (e.g., 0.3 mm$^2$ to 0.6 mm$^2$) may be easily visible to the naked eye. However, if the color contrast between the opaque, microporous region and any underlying layer beneath the any individual see-through area of lower porosity is relatively small, it may be desirable to have larger individual see-through areas (e.g., larger than 0.6 mm$^2$).

The fastening tape according to the present disclosure can be converted to any desired size and shape. The fastening tape may be in the form of a fastening tab as shown in FIGS. 1, 1A, and 1B, or the fastening tape may be attached on the ears of a personal hygiene article. Also, the mechanical fastener according to the present disclosure can be converted to any desired size and shape. For example, a personal hygiene article having ears may include a larger patch of male fastening elements relative to a mechanical fastener patch on a fastening tab. Also, a personal hygiene article can have two smaller target zones of loop material along the longitudinal edges of the back sheet instead of the large target area 68 shown in FIG. 1.

In the open configuration shown in FIG. 1A, the geometry of the tape backing 75 and the release tape 79 results in a Y-shaped bond being formed around the diaper edge in the rear waist region 65, which is often referred to in the industry as a Y-bond. However, other configurations of a release surface on a fastening tape are possible, which fastening tapes may or may not include a mechanical fastener. For example, a fastening tape may be partially coated on its second surface with a release coating (e.g., a silicone, fluorochemical, or carbamate coating) and partially coated on its first surface with an adhesive. A fastening tab may be cut from such a tape and attached through its proximal end to the edge of a diaper with its release surface exposed. A distal end of the tab may be folded into a loop so that the adhesive is in contact with the release coating. Such a configuration is described in U.S. Pat. No. 3,930,502 (Tritsch). In another example, the fastening tape may be partially coated with a release coating and partially coated with an adhesive on the same surface. A fastening tab may be cut from the tape and attached through its proximal end to the edge of a diaper with adhesive on its distal end, and the distal end of the tab may be folded back onto itself so that the adhesive is in contact with the release coating. The tape backing may be a continuous piece as shown at 75 in FIG. 1A, or when a stretchable film is desired, for example, there may be two pieces of a backing both attached to an elastic film as described in Int. Pat. Appl. Pub. No. WO 2004/075803 (Loescher et al.). Still other useful configurations of fastening tabs are described in U.S. Pat. Appl. Pub. No. 2007/0286976 (Selen et al.)

The adhesive 76 in any of the embodiments of the fastening tape according to the present disclosure is generally made up of an adhesive having a peel strength that is sufficient to permanently attach the tape backing 75 to the outside surface of an absorbent article and, in some embodiments, to permanently attach the mechanical fastener 80 to the tape backing 75. The adhesive used may be any conventional adhesive, including pressure sensitive adhesives (PSAs) and non-pressure sensitive adhesives. PSAs are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Suitable pressure sensitive adhesives include acrylic resin and natural or synthetic rubber-based adhesives and may be hot melt pressure sensitive adhesives. Illustrative rubber based adhesives include styrene-isoprene-styrene, styrene-butadiene-styrene, styrene-ethylene/butylene-styrene, and styrene-ethylene/propylene-styrene that may optionally contain diblock components such as styrene isoprene and styrene butadiene. The adhesive may be applied using hot-melt, solvent, or emulsion techniques.

In personal hygiene articles according to the present disclosure and/or incorporating a fastening tape or mechanical fastener according to the present disclosure, such as that shown in FIG. 1, the topsheet 61 is typically permeable to liquid and designed to contact a wearer's skin, and the outwardly facing backsheet 62 is typically impermeable to liquids. There is typically an absorbent core 63 encased between the topsheet and the backsheet. Various materials can be useful for the topsheet 61, the backsheet 62, and the absorbent core 63 in an absorbent article according to the present disclosure. Examples of materials useful for topsheets 61 include apertured plastic films, woven fabrics, nonwoven webs, porous foams, and reticulated foams. In some embodiments, the topsheet 61 is a nonwoven material. Examples of suitable nonwoven materials include spunbond or meltblown webs of fiber forming polymer filaments (e.g., polyolefin, polyester, or polyamide filaments) and bonded carded webs of natural polymers (e.g., rayon or cotton fibers) and/or synthetic polymers (e.g., polypropylene or polyester fibers). The nonwoven web can be surface treated with a surfactant or otherwise processed to impart the desired level of wettability and hydrophilicity. The backsheet 62 is sometimes referred to as the outer cover and is the farthest layer from the user. The backsheet 62 functions to prevent body exudates contained in absorbent core from wetting or soiling the wearer's clothing, bedding, or other materials contacting the diaper. The backsheet 62 can be a thermoplastic film (e.g., a poly(ethylene) film). The thermoplastic film may be embossed and/or matte finished to provide a more aesthetically pleasing appearance. The backsheet 62 can also include woven or nonwoven fibrous webs, for example, laminated to the thermoplastic films or constructed or treated to impart a desired level of liquid impermeability even in the absence of a thermoplastic film. Suitable backsheets 62 also include vapor or gas permeable microporous "breathable" materials that are substantially impermeable to liquid. Suitable absorbent cores 63 include natural, synthetic, or modified natural polymers that can absorb and hold liquids (e.g., aqueous liquids). Such polymers can be crosslinked (e.g., by physical entanglement, crystalline domains, covalent bonds, ionic complexes and associations, hydrophilic associations such as hydrogen bonding, and hydrophobic associations or Van der Waals forces) to render them water insoluble but swellable. Such absorbent materials are usually designed to quickly absorb liquids and hold them, usually without release. Examples of suitable absorbent materials useful in absorbent articles disclosed herein include wood pulp or other cellulosic materials and super absorbent polymers (SAP).

Personal hygiene articles (e.g., incontinence articles and diapers) according to the present disclosure and/or including a fastening tape or mechanical fastener disclosed herein may have any desired shape such as a rectangular shape, a shape like the letter I, a shape like the letter T, or an hourglass shape. The personal hygiene article may also be a refastenable pants-style diaper with fastening tabs 70 along each longitudinal edge. In some embodiments, including the embodiment shown in FIG. 1, the topsheet 61 and backsheet 62 are attached to each other and together form chassis all the way out to the first and second longitudinal opposing edges 64a and 64b. In some embodiments, only one of the topsheet 61 or the backsheet 62 extends to the first and second longitudinal opposing edges 64a and 64b. In other embodiments, the chassis can include separate side panels that are attached to the sandwich of at least topsheet 61, backsheet 62, and absorbent core 63 during manufacturing of the absorbent article, for example, to form ear portions. The side panels can be made of a material that is the same as the topsheet 61 or backsheet 62 or may be made from a different material (e.g., a different nonwoven). In these embodiments, the side panels also form part of the chassis.

The personal hygiene article according to the present disclosure also includes sanitary napkins. A sanitary napkin typically includes a backsheet that is intended to be placed adjacent to the wearer's undergarment. Adhesive or mechanical fasteners are provided on the backsheet to attach the sanitary napkin to the wearer's undergarment. The sanitary napkin typically also includes a topsheet and absorbent core. The backsheet, topsheet, and absorbent core can be made from any of the materials described above for these components in diapers or incontinence articles. The sanitary napkin may have any desired shape such as an hourglass, keyhole, or generally rectangular shape. The backsheet may also include flaps that are intended to wrap around to the opposite side of the wearer's undergarment. The backsheet includes a microporous film having an opaque, microporous region and at least one see-through region of lower porosity within the opaque, microporous region. The see-through region of lower porosity or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

Figure 2:
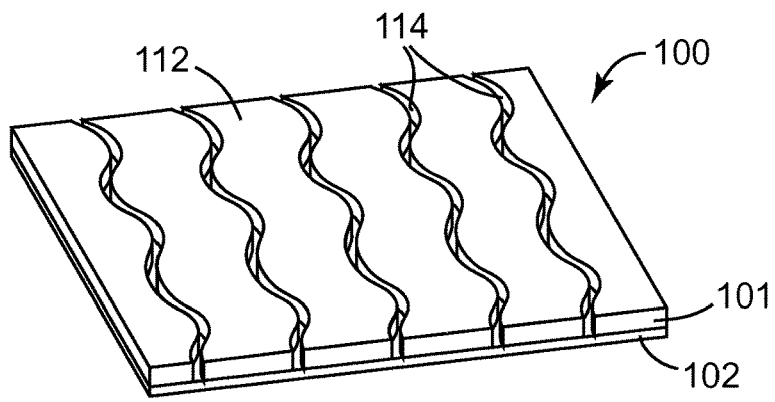
FIG. 2 is a perspective view of an embodiment of a laminate in which the microporous film useful in various embodiments of the present disclosure is a layer.

In some embodiments, the microporous film in the fastening tape or mechanical fastener according to the present disclosure is a first layer of a multilayer construction comprising the first layer and a second layer, and a portion of the second layer is visible through the at least one see-through region of lower porosity in the microporous film. FIG. 2 is a perspective view of a multilayer construction 100 in which the microporous film is a first layer 101. The microporous film has an opaque, microporous region 112 and a repeating series of see-through regions of lower porosity 114. The second layer 102 of the multilayer construction 100 is visible through the see-through regions 114. The microporous film may be a tape backing, release tape, or mechanical fastener as described above, and the mechanical fastener may include male or female fastening elements. The repeating series of see-through regions of lower porosity 114 may be made by a number of useful methods. For example, a nip made from two heated rolls in which one of the rolls has raised areas in the shape of the see-through regions 114 may be useful. The heat and pressure in the nip can collapse the microporous structure in the raised areas to form the see-through regions. The second layer 102 of the multilayer construction 100 may have a contrasting color that is visible between the see-through regions 114.

A multilayer construction such as that shown in FIG. 2 can be made in various ways, and the second layer 102 or other layers can be made from a variety of materials. In some embodiments, the second layer or other layers may comprise woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. The second layer 102 or other layers may be colored (e.g., by inclusion of a pigment or dye). The second layer 102 or other layers may also be metalized. For any of these types of materials, the first and second layer can be joined by extrusion lamination, adhesives (e.g., pressure sensitive adhesives), or other bonding methods (e.g., ultrasonic bonding, compression bonding, or surface bonding). For example, in the case of plastic films, a first and second layer can be extruded separately and then laminated together. In some embodiments, the multilayer construction is a multilayer film made, for example, by coextrusion. A multilayer film of at least first and second layers can be coextruded using any suitable type of coextrusion die and any suitable method of film making such as blown film extrusion or cast film extrusion. In some embodiments, a multilayer melt stream can be formed by a multilayer feedblock, such as that shown in U.S. Pat. No. 4,839,131 (Cloeren). For the best performance in coextrusion, the polymeric compositions for each layer can be chosen to have similar properties such as melt viscosity. Techniques of coextrusion are found in many polymer processing references, including Progelhof, R. C., and Throne, J. L., "Polymer Engineering Principles", Hanser/Gardner Publications, Inc., Cincinnati, Ohio, 1993. In some embodiments, a first layer including a beta-nucleating agent, diluent, or cavitating agent as described below in a first polymeric composition can be coextruded with a second, different polymeric composition, lacking such an agent. The second polymeric composition may include a colorant such as a pigment or dye. Stretching the coextruded film can make the first layer opaque and microporous, effectively hiding the color in the second layer until the see-through region described herein is formed to reveal a portion of the second layer.

A multilayer film according to the present disclosure may have more than one microporous layer made by any of the methods described below. For example, a single second layer can have microporous layers on both of its surfaces. The single second layer may be colored. In other embodiments, multiple, different-colored layers may be interleaved with multiple microporous layers in an alternating fashion. In some embodiments, see-through regions of lower porosity are then made in certain of the microporous layers to reveal different colors in one or more see-through regions. Multilayer films such as these can be attached on one side of a clear tape backing or release tape in the fastening tapes disclosed herein. In these embodiments, the tape backing and release tape may be multilayered.

Referring again to FIG. 2, in which the microporous film is a first layer 101 of a multilayer construction 100 comprising the first layer 101 and a second layer 102, and a portion of the second layer is visible through the at least one see-through region of lower porosity in the microporous film, the second layer 102 may be a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A similar process that also includes co-extruding a continuous outer skin layer on one or both outer faces of the side-by-side co-extruded film as described in U.S. Pat. No. 6,669,887 (Hilston et al.) may also be useful. Management of the flow of different polymer compositions into side-by-side lanes can also be carried out using a single manifold die with a distribution plate in contrast to approaches that require multiple dies to achieve side-by-side co-extrusion. Further details about the die and the distribution plate can be found, for example, in U.S. Pat. Appl. Pub. No. 2012/0308755 (Gorman et al.). Side-by-side co-extruded films can also be made by other extrusion dies that comprise a plurality of shims and have two cavities for molten polymer, such as those dies described, for example, in Int. Pat. App. Pub. No. WO 2011/119323 (Ausen et al.) and U.S. Pat. App. Pub. No. 2014/0093716 (Hanschen et al.). Extrusion dies for side-by-side co-extrusion are also available from Nordson Extrusion Dies Industries, Chippewa Falls, Wis. The side-by-side coextruded film may have different colors or different shades of the same color in different lanes so that more than one color can be seen through the see-through regions of lower porosity 114.

Figure 3:
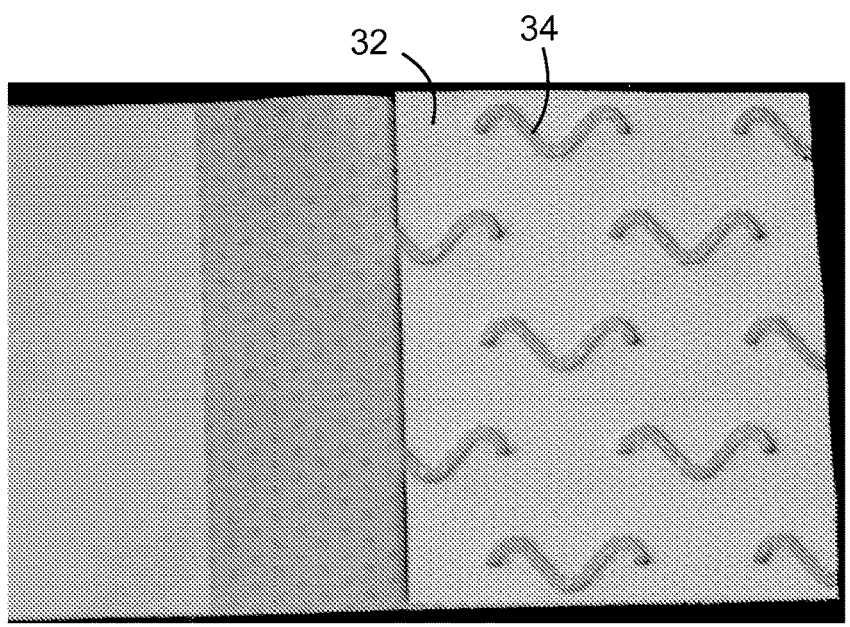
FIG. 3 is a photograph of an embodiment of a mechanical fastener according to the present disclosure.

A photograph of an embodiment of a fastening tape and mechanical fastener according to the present disclosure is shown in FIG. 3. In this embodiment, the mechanical fastener, which includes male fastening elements, is a microporous film. The microporous film has a repeating pattern of see-through regions of lower porosity 34 within a microporous region 32 of the microporous film. In the illustrated embodiment, the mechanical fastener is adhered to a nonwoven backing. Although not shown in the photograph, the nonwoven backing has a color, while the microporous film is white in the microporous regions. The color of the nonwoven backing can be seen through the see-through regions.

Figure 4:
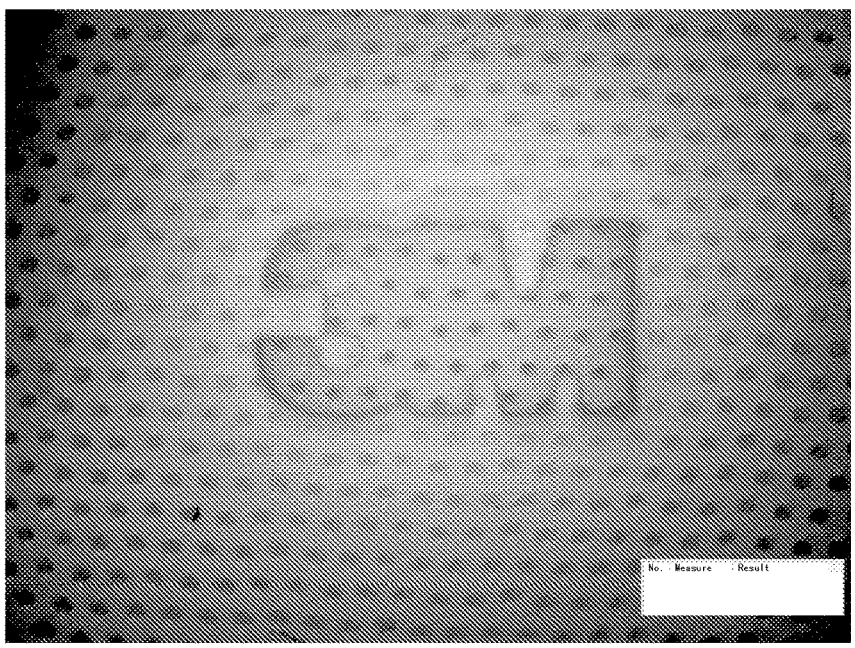
FIG. 4 is a photograph of another embodiment of a mechanical fastener according to the present disclosure.

Another photograph of an embodiment of a mechanical fastener according to the present disclosure is shown in FIG. 4. In this embodiment, the mechanical fastener, which includes male fastening elements, is a microporous film. The microporous film has a trademark of 3M Company, St. Paul, Minn., made digitally with a laser. The laser-formed trademark forms the see-through region of lower porosity within a microporous region of the microporous film.

Figure 5:
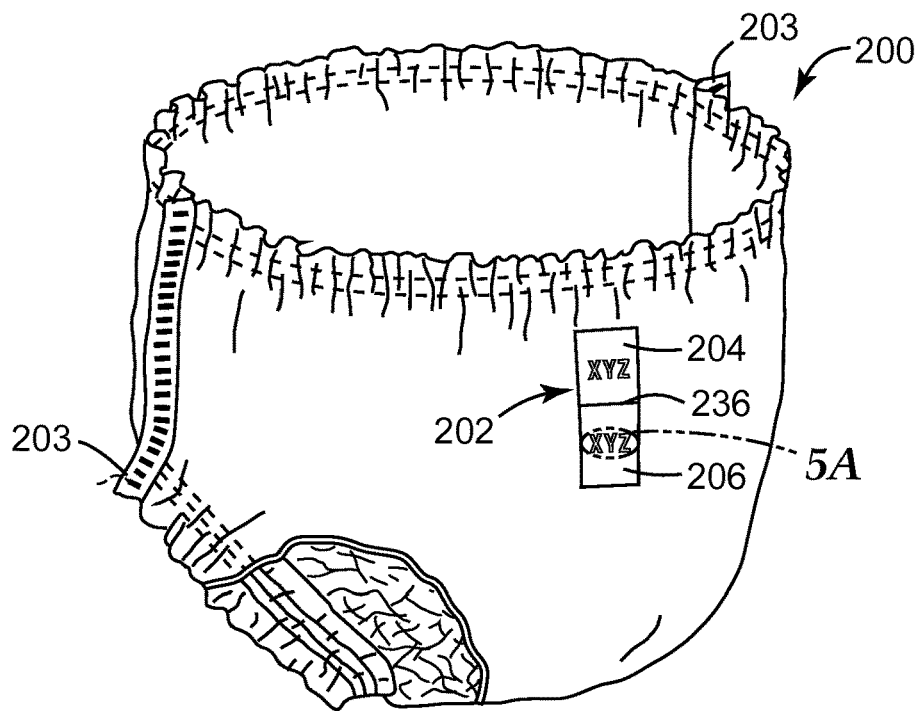
FIG. 5 is a perspective view of an embodiment of personal hygiene article incorporating a fastening tape and/or mechanical fastener according to the present disclosure, in which the fastening tape is useful as a disposal tape.
Figure 5A:
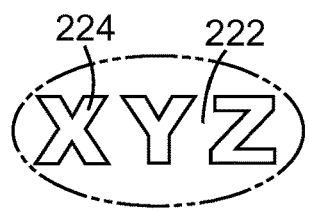
FIG. 5A is an expanded view of the indicated area in FIG. 5.
Figure 5B:
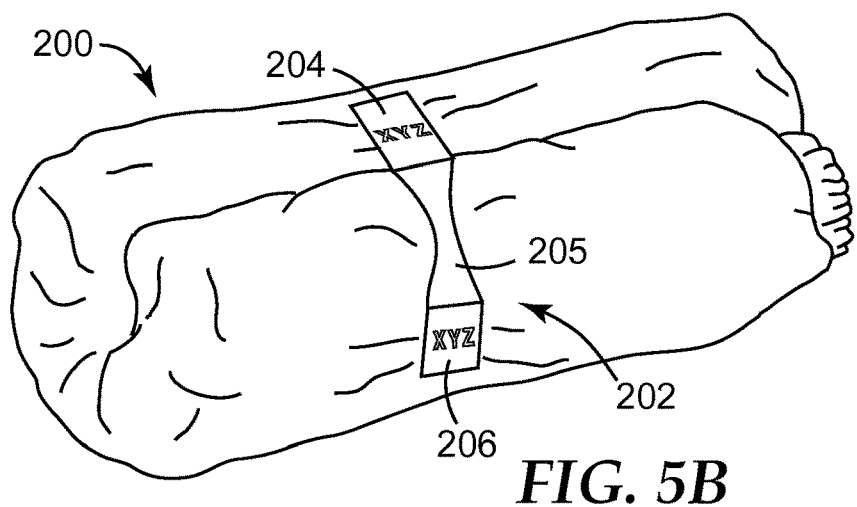
FIG. 5B is a perspective view of the personal hygiene article shown in FIG. 5 rolled up and ready for disposal.

Another embodiment of a fastening tape according to the present disclosure is shown in FIGS. 5, 5A, and 5B in connection with a pants or shorts style incontinence article 200, which may be an infant diaper or adult incontinence article. After use of such a pants style incontinence article, it is typically torn apart along at least one of its seams 203 before rolling it up so that it does not have to be removed over the legs. The fastening tape according to the present disclosure is in the form of disposal tape 202 in the illustrated embodiment. It should be understood that the term "fastening tape" as used herein includes disposal tape. Disposal tape 202 is used to hold a used (soiled) incontinence article in a rolled-up configuration after it has been torn along the seams 203 as shown in FIG. 5B. Although a variety of disposal tape constructions may be useful, in the illustrated embodiment, the disposal tape 202 includes two adjacent first and second tape tab elements 204, 206 separated by slit 236. Each of the first and second tape tab element 204,206 is adhesively attached to a plastically deformable film 205, which is visible in FIG. 5A. More details about this disposal tape construction can be found in Int. Pat. Appl. Pub. No. WO 2007/032965 (Dahm et al.). In the illustrated embodiment, the tape tab elements 204, 206 each comprise a microporous film having an opaque, microporous region 222 and see-through regions of lower porosity 224 within the opaque, microporous region 222. The see-through regions of lower porosity 224 are in the form of alphabetical letters in the illustrated embodiment. However, as described above, the see-through regions can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

Various methods are useful for making the microporous film disclosed herein. In some embodiments, the porosity in the microporous film, which may be the tape backing, the release tape, or the mechanical fastener in the various embodiments disclosed herein, results from beta-nucleation. Semi-crystalline polyolefins can have more than one kind of crystal structure. For example, isotactic polypropylene is known to crystallize into at least three different forms: alpha (monoclinic), beta (pseudohexangonal), and gamma (triclinic) forms. In melt-crystallized material the predominant form is the alpha or monoclinic form. The beta form generally occurs at levels of only a few percent unless certain heterogeneous nuclei are present or the crystallization has occurred in a temperature gradient or in the presence of shearing forces. The heterogeneous nuclei are typically known as beta-nucleating agents, which act as foreign bodies in a crystallizable polymer melt. When the polymer cools below its crystallization temperature (e.g., a temperature in a range from 60° C. to 120° C. or 90° C. to 120° C.), the loose coiled polymer chains orient themselves around the beta-nucleating agent to form beta-phase regions. The beta form of polypropylene is a meta-stable form, which can be converted to the more stable alpha form by thermal treatment and/or applying stress. Micropores can be formed in various amounts when the beta-form of polypropylene is stretched under certain conditions; see, e.g., Chu et al., "Microvoid formation process during the plastic deformation of β-form polypropylene", *Polymer*, Vol. 35, No. 16, pp. 3442-3448, 1994, and Chu et al., "Crystal transformation and micropore formation during uniaxial drawing of β-form polypropylene film", *Polymer*, Vol. 36, No. 13, pp. 2523-2530, 1995. Pore sizes achieved from this method can range from about 0.05 micrometer to about 1 micrometer, in some embodiments, about 0.1 micrometer to about 0.5 micrometer.

Generally, when the porosity in the microporous film is generated from a beta-nucleating agent, the film comprises a semi-crystalline polyolefin. Various polyolefins may be useful. Typically the semi-crystalline polyolefin comprises polypropylene. It should be understood that a semi-crystalline polyolefin comprising polypropylene may be a polypropylene homopolymer or a copolymer containing propylene repeating units. The copolymer may be a copolymer of propylene and at least one other olefin (e.g., ethylene or an alpha-olefin having from 4 to 12 or 4 to 8 carbon atoms). Copolymers of ethylene, propylene and/or butylenes may be useful. In some embodiments, the copolymer contains up to 90, 80, 70, 60, or 50 percent by weight of polypropylene. In some embodiments, the copolymer contains up to 50, 40, 30, 20, or 10 percent by weight of at least one of polyethylene or an alpha-olefin. The semi-crystalline polyolefin may also be part of a blend of thermoplastic polymers that includes polypropylene. Suitable thermoplastic polymers include crystallizable polymers that are typically melt processable under conventional processing conditions. That is, on heating, they will typically soften and/or melt to permit processing in conventional equipment, such as an extruder, to form a sheet. Crystallizable polymers, upon cooling their melt under controlled conditions, spontaneously form geometrically regular and ordered chemical structures. Examples of suitable crystallizable thermoplastic polymers include addition polymers, such as polyolefins. Useful polyolefins include polymers of ethylene (e.g., high density polyethylene, low density polyethylene, or linear low density polyethylene), an alpha-olefin (e.g, 1-butene, 1-hexene, or 1-octene), styrene, and copolymers of two or more such olefins. The semi-crystalline polyolefin may comprise mixtures of stereo-isomers of such polymers, e.g., mixtures of isotactic polypropylene and atactic polypropylene or of isotactic polystyrene and atactic polystyrene. In some embodiments, the semi-crystalline polyolefin blend contains up to 90, 80, 70, 60, or 50 percent by weight of polypropylene. In some embodiments, the blend contains up to 50, 40, 30, 20, or 10 percent by weight of at least one of polyethylene or an alpha-olefin.

In some embodiments, the microporous film is made from a polymeric composition comprising a semi-crystalline polyolefin and having a melt flow rate in a range from 0.1 to 10 decigrams per minute, for example, 0.25 to 2.5 decigrams per minute.

When the porosity in the microporous film is generated from a beta-nucleating agent, the beta-nucleating agent may be any inorganic or organic nucleating agent that can produce beta-spherulites in a melt-formed sheet comprising polyolefin. Useful beta-nucleating agents include gamma quinacridone, an aluminum salt of quinizarin sulphonic acid, dihydroquinoacridin-dione and quinacridin-tetrone, triphenenol ditriazine, calcium silicate, dicarboxylic acids (e.g., suberic, pimelic, ortho-phthalic, isophthalic, and terephthalic acid), sodium salts of these dicarboxylic acids, salts of these dicarboxylic acids and the metals of Group IIA of the periodic table (e.g., calcium, magnesium, or barium), delta-quinacridone, diamides of adipic or suberic acids, different types of indigosol and cibantine organic pigments, quiancridone quinone, N',N'-dicyclohexil-2,6-naphthalene dicarboxamide (available, for example, under the trade designation "NJ-Star NU-100" from New Japan Chemical Co. Ltd.), antraquinone red, and bis-azo yellow pigments. The properties of the extruded film are dependent on the selection of the beta nucleating agent and the concentration of the beta-nucleating agent. In some embodiments, the beta-nucleating agent is selected from the group consisting of gamma-quinacridone, a calcium salt of suberic acid, a calcium salt of pimelic acid and calcium and barium salts of polycarboxylic acids. In some embodiments, the beta-nucleating agent is quinacridone colorant Permanent Red E3B, which is also referred to as Q-dye. In some embodiments, the beta-nucleating agent is formed by mixing an organic dicarboxylic acid (e.g., pimelic acid, azelaic acid, o-phthalic acid, terephthalic acid, and isophthalic acid) and an oxide, hydroxide, or acid salt of a Group II metal (e.g., magnesium, calcium, strontium, and barium). So-called two component initiators include calcium carbonate combined with any of the organic dicarboxylic acids listed above and calcium stearate combined with pimelic acid. In some embodiments, the beta-nucleating agent is aromatic tri-carboxamide as described in U.S. Pat. No. 7,423,088 (Mader et al.).

The beta-nucleating agent serves the important functions of inducing crystallization of the polymer from the molten state and enhancing the initiation of polymer crystallization sites so as to speed up the crystallization of the polymer. Thus, the nucleating agent may be a solid at the crystallization temperature of the polymer. Because the nucleating agent increases the rate of crystallization of the polymer, the size of the resultant polymer particles, or spherulites, is reduced.

A convenient way of incorporating beta-nucleating agents into a semi-crystalline polyolefin useful for making a microporous film disclosed herein is through the use of a concentrate. A concentrate is typically a highly loaded, pelletized polypropylene resin containing a higher concentration of nucleating agent than is desired in the final microporous film. The nucleating agent is present in the concentrate in a range of 0.01% to 2.0% by weight (100 to 20,000 ppm), in some embodiments in a range of 0.02% to 1% by weight (200 to 10,000 ppm). Typical concentrates are blended with non-nucleated polyolefin in the range of 0.5% to 50% (in some embodiments, in the range of 1% to 10%) by weight of the total polyolefin content of the microporous film. The concentration range of the beta-nucleating agent in the final microporous film may be 0.0001% to 1% by weight (1 ppm to 10,000 ppm), in some embodiments, 0.0002% to 0.1% by weight (2 ppm to 1000 ppm). A concentrate can also contain other additives such as stabilizers, pigments, and processing agents.

The level of beta-spherulites in the semi-crystalline polyolefin can be determined, for example, using X-ray crystallography and Differential Scanning calorimetry (DSC). By DSC, melting points and heats of fusion of both the alpha phase and the beta phase can be determined in a microporous film useful for practicing the present disclosure. For semi-crystalline polypropylene, the melting point of the beta phase is lower than the melting point of the alpha phase (e.g., by about 10 to 15 degrees Celsius). The ratio of the heat of fusion of the beta phase to the total heat of fusion provides a percentage of the beta-spherulites in a sample. The level of beta-spherulites can be at least 10, 20, 25, 30, 40, or 50 percent, based on the total amount of alpha and beta phase crystals in the film. These levels of beta-spherulites may be found in the film before it is stretched.

In some embodiments, the microporous film useful for practicing the present disclosure in any of its embodiments is formed using a thermally induced phase separation (TIPS) method. This method of making the microporous film typically includes melt blending a crystallizable polymer and a diluent to form a melt mixture. The melt mixture is then formed into a film and cooled to a temperature at which the polymer crystallizes, and phase separation occurs between the polymer and diluent, forming voids. In this manner a film is formed that comprises an aggregate of crystallized polymer in the diluent compound. The voided film has some degree of opacity.

In some embodiments, following formation of the crystallized polymer, the porosity of the material is increased by at least one of stretching the film in at least one direction or removing at least some of the diluent. This step results in separation of adjacent particles of polymer from one another to provide a network of interconnected micropores. This step also permanently attenuates the polymer to form fibrils, imparting strength and porosity to the film. The diluent can be removed from the material either before or after stretching. In some embodiments, the diluent is not removed. Pore sizes achieved from this method can range from about 0.2 micron to about 5 microns.

When the microporous film useful for practicing the present disclosure is made from a TIPS process, including embodiments in which the microporous film is the tape backing, the release tape, or the mechanical fastener, the film can comprise any of the semi-crystalline polyolefins described above in connection with films made by beta-nucleation. In addition, other crystallizable polymers that may be useful alone or in combination include high and low density polyethylene, poly(vinylidine fluoride), poly(methyl pentene) (e.g., poly(4-methylpentene), poly(lactic acid), poly(hydroxybutyrate), poly(ethylene-chlorotrifluoroethylene), poly(vinyl fluoride), polyvinyl chloride, poly(ethylene terephthalate), polybutylene terephthalate), ethylene-vinyl alcohol copolymers, ethylene-vinyl acetate copolymers, polybuyltene, polyurethanes, and polyamides (e.g., nylon-6 or nylon-66). Useful diluents for providing the microporous film according to the present disclosure include mineral oil, mineral spirits, dioctylphthalate, liquid paraffins, paraffin wax, glycerin, petroleum jelly, polyethylene oxide, polypropylene oxide, polytetramethylene oxide, soft carbowax, and combinations thereof. The quantity of diluent is typically in a range from about 20 parts to 70 parts, 30 parts to 70 parts, or 50 parts to 65 parts by weight, based upon the total weight of the polymer and diluent.

In some embodiments, the microporous film useful for practicing the present disclosure in any of its embodiments is formed using particulate cavitating agents. Such cavitating agents are incompatible or immiscible with the polymeric matrix material and form a dispersed phase within the polymeric core matrix material before extrusion and orientation of the film. When such a polymer substrate is subjected to uniaxial or biaxial stretching, a void or cavity forms around the distributed, dispersed-phase moieties, providing a film having a matrix filled with numerous cavities that provide an opaque appearance due to the scattering of light within the matrix and cavities. The microporous film, including embodiments in which the microporous film is the tape backing, the release tape, or the mechanical fastener, can comprise any of the polymers described above in connection with TIPS films. The particulate cavitating agents may be inorganic or organic. Organic cavitating agents generally have a melting point that is higher than the melting point of the film matrix material. Useful organic cavitating agents include polyesters (e.g., polybutylene teraphthalate or nylon such as nylon-6), polycarbonate, acrylic resins, and ethylene norbornene copolymers. Useful inorganic cavitating agents include talc, calcium carbonate, titanium dioxide, barium sulfate, glass beads, glass bubbles (that is, hollow glass spheres), ceramic beads, ceramic bubbles, and metal particulates. The particle size of cavitating agents is such that at least a majority by weight of the particles comprise an overall mean particle diameter, for example, of from about 0.1 micron to about 5 microns, in some embodiments, from about 0.2 micron to about 2 microns. (The term "overall" refers to size in three dimensions; the term "mean" is the average.) The cavitating agent may be present in the polymer matrix in an amount of from about 2 weight percent to about 40 weight percent, about 4 weight percent to about 30 weight percent, or about 4 weight percent to about 20 weight percent, based upon the total weight of the polymer and cavitating agent.

In any of the embodiments of the microporous film described above in which the microporous film is a release tape in the fastening tape according to the present disclosure, the microporous film is typically provided with a release coating (e.g., a silicone, fluorochemical, or carbamate coating).

Additional ingredients may be included in the microporous film useful for practicing any of the embodiments of the present disclosure, depending on the desired application. For example, surfactants, antistatic agents, ultraviolet radiation absorbers, antioxidants, organic or inorganic colorants, stabilizers, flame retardants, fragrances, nucleating agents other than a beta-nucleating agent, and plasticizers may be included. Many of the beta-nucleating agents described above have a color. Also, colorants may be added, for example, in the form of a color concentrate or a colored master batch.

For the microporous films made by any of the methods described above, the film is typically stretched to form or enhance the microporous structure. Stretching the film can be carried out on a web biaxially or monoaxially. Biaxial stretching means stretching in two different directions in the plane of the backing. Typically, but not always, one direction is the machine direction or longitudinal direction "L", and the other, different direction is the cross direction or width direction "W". Biaxial stretching can be performed sequentially by stretching the thermoplastic backing, for example, first in one of the longitudinal or width direction and subsequently in the other of the longitudinal or width direction. Biaxial stretching can also be performed essentially simultaneously in both directions. Monoaxial stretching refers to stretching in only one direction in the plane of the backing. Typically, monoaxial stretching is performed in one of the "L" or "W" direction but other stretch directions are also possible.

In some embodiments, the stretching increases at least one of the film's length ("L") or width ("W") at least 1.2 times (in some embodiments, at least 1.5, 2, or 2.5 times). In some embodiments, the stretching increases both of the film's length ("L") and width ("W") at least 1.2 times (in some embodiments, at least 1.5, 2, or 2.5 times). In some embodiments, the stretching increases at least one of the film's length ("L") or width ("W") up to 5 times (in some embodiments, up to 2.5 times). In some embodiments, the stretching increases both of the film's length ("L") and width ("W") up to 5 times (in some embodiments, up to 2.5 times). In films containing a beta-nucleating agent as described above that include upstanding posts (e.g., of male fastening elements), it has unexpectedly been found that even monoaxial stretching at a stretch ratio of up to 2.5, 2.25, 2.2, or even 2 can provide high levels of porosity and opacity even in the absence of other cavitating agents such as calcium carbonate. In films that do not include upstanding posts, the stretching increases at least one of the film's length ("L") or width ("W") up to 10 times (in some embodiments, up to 20 times or more). In some embodiments, the stretching increases both of the film's length ("L") and width ("W") up to 10 times (in some embodiments, up to 20 times or more).

In general, when a thermoplastic film is monoaxially or biaxially stretched at a temperature below the melting point of the thermoplastic material, particularly at a temperature below the line drawing temperature of the film, the thermoplastic film may stretch non-uniformly, and a clear boundary is formed between stretched and unstretched parts. This phenomenon is referred to as necking or line drawing. However, substantially the entire thermoplastic backing is stretched uniformly when it is stretched to a sufficiently high degree. The stretch ratio at which this occurs is referred to as the "natural stretch ratio" or "natural draw ratio." Stretching above the natural stretch ratio is understood to provide significantly more uniform properties or characteristics such as thickness, tensile strength, and modulus of elasticity. For any given thermoplastic backing and stretch conditions, the natural stretch ratio is determined by factors such as the composition of the thermoplastic resin forming the thermoplastic backing, the morphology of the formed thermoplastic backing due to quenching conditions on the tool roll, for example, and temperature and rate of stretching. Furthermore, for biaxially stretched thermoplastic backings, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in the first direction and one in the second direction) which result in the natural stretch ratio. The term "stretch ratio" refers to ratio of a linear dimension of a given portion of the thermoplastic backing after stretching to the linear dimension of the same portion before stretching. The natural stretch ratio of the most common crystalline form of polypropylene, the alpha form, has been reported to be about 6:1.

Stretching the film useful for practicing the present disclosure can be carried out in a variety of ways. When the film is a web of indefinite length, for example, monoaxial stretching in the machine direction can be performed by propelling the film over rolls of increasing speed. The term "machine direction" (MD) as used herein denotes the direction of a running, continuous web of the film. A versatile stretching method that allows for monoaxial, sequential biaxial, and simultaneous biaxial stretching of the film employs a flat film tenter apparatus. Such an apparatus grasps the thermoplastic web using a plurality of clips, grippers, or other film edge-grasping means along opposing edges of the film in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. The term "cross-direction" (CD) as used herein denotes the direction which is essentially perpendicular to the machine direction. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany.

Stretching the film is typically performed at elevated temperatures, for example, up to 150° C. Heating the film may allow it to be more flexible for stretching. Heating can be provided, for example, by IR irradiation, hot air treatment or by performing the stretching in a heat chamber. In some embodiments of the mechanical fastener according to the present disclosure, heating is only applied to a second surface of the film opposite the first surface from which the mechanical fastening elements project to minimize any damage to the mechanical fastening elements that may result from heating. For example, in these embodiments, only rollers that are in contact with the second surface of the film are heated. In some embodiments, stretching the film is carried out at a temperature range from 50° C. to 130° C.

In the fastening tape and mechanical fastener according to the present disclosure, the film may have a variety of thicknesses. For example, the initial thickness (i.e., before any stretching) of the film may be up to about 750, 500, 400, 250, or 150 micrometers, depending on the desired application. In some embodiments, the initial thickness of the film is at least about 50, 75, or 100 micrometers, depending on the desired application. In some embodiments, the initial thickness of the film is in a range from 50 to about 225 micrometers, from about 75 to about 200 micrometers, or from about 100 to about 150 micrometers. The film may have an essentially uniform cross-section, or, in the case of mechanical fasteners, the film may have structure beyond what is provided by the upstanding posts, which may be imparted, for example, by at least one of the forming rolls described below.

In some embodiments, stretching a film described above in order to form or enhance microporosity provides an increase in opacity of at least 10, 15, 20, 25, or 30 percent. The increase in opacity may be, for example, up to 90, 85, 80, 75, 70, 65, 60, 55, or 50 percent. The initial opacity is affected, for example, by the thickness of the film. Stretching a film typically results in a decrease in thickness, which would typically lead to a decrease in opacity. However, stress whitening and micropore formation leads to an increase in opacity. For the purposes of the present disclosure, opacity can be measured using a spectrophotometer with the "L" value measured separately against a black background and against a white background, respectively. The opacity is calculated as (L measured against the black background/L measured against the white background) times 100. The "L" value is one of three standard parameters in the CIELAB color space scale established by the International Commission on Illumination. "L" is a brightness value, ranging from 0 (black) to 100 (highest intensity). A percentage change in opacity that results from stretching is calculated by [(opacity after stretching−opacity before stretching)/opacity before stretching] times 100.

In some embodiments, stretching a film described above in order to form or enhance microporosity provides a decrease in the grayscale value of the film of at least twenty percent. In some embodiments, stretching provides a decrease in a grayscale value of at least 25, 30, 40, or 50 percent. The decrease in grayscale value may be, for example, up to 90, 85, 80, 75, 70, 65, or 60 percent. For the purposes of this disclosure, the grayscale value is measured in transmission mode using the method described in the Example section, below. Stretching a film typically results in a decrease in thickness, which would typically lead to an increase in the grayscale value measured in transmission mode. However, stress whitening and micropore formation leads to decrease in transmission mode grayscale values. A percentage change in grayscale value that results from stretching the film is calculated by [(grayscale value after stretching−grayscale value before stretching)/grayscale value before stretching] times 100. In some embodiments, the microporous film has a grayscale value of up to 40 (in some embodiments, up to 35, 30, 25, 20 or 15). In some embodiments, the grayscale values for the microporous films disclosed herein are comparable or better than those achieved for polyolefin films of similar composition but incorporating conventional amounts of IR blocking agents such as titanium dioxide.

The opacity and grayscale measurement of the microporous film relate to its ability to transmit light. As used herein, the term "light" refers to electromagnetic radiation, whether visible to the unaided human eye or not. Ultraviolet light is light having a wavelength in a range from about 250 nanometers (nm) to 380 nm. Visible light is light having a wavelength in a range from 380 nanometers (nm) to 700 nm. Infrared light has a wavelength in a range from about 700 nm to 300 micrometers. After the microporous film useful for practicing the present disclosure has been stretched, it has decreased transmission to ultraviolet, visible, and infrared light. The micropores in the stretched film tend to scatter light in the ultraviolet, visible, and infrared ranges.

As described above, heat, pressure, or a combination thereof may be useful for providing the see-through regions. Typically, the at least one see-through region of lower porosity is heated to the melting temperature of the thermoplastic in the microporous film. Melting the microporous film in the at least one see-through region results in a permanent change in the structure of the film in the see-through region, which can be accompanied by some film shrinkage in that region. Heating can be carried out in a press or a heated nip having a raised image of the at least one see-through region so that pressure accompanies the heating to collapse the microporous structure. Pressure alone may provide a temporary change in the microporous structure of the microporous film in some instances. When using a static press, it can be useful to use a rubber surface on the film side opposite the side that is exposed to the raised and heated image. The rubber surface can prevent two hard surfaces from forming a hole in the film while the see-through region is being made. In a nip, the pressure and gap can be adjusted as well as the line speed to prevent forming holes in the film.

Heating may also be carried out with hot air or with a directed radiation source such as a laser. A variety of different types of laser may be useful. For example, a carbon dioxide laser may be useful. An ultraviolet laser and diode laser may also be useful. Suitable wavelengths for the laser can in a range from 200 nm to 11,000 nm. The laser wavelength and absorption properties of the material can be selected to be matched or nearly matched so as to create the heating of material. For a person skilled in the art, the suitable power for the laser, beam size on the material, and speed of the beam movement across the material can be adjusted to achieve the desired heating. This matching of laser and material can be advantageous, for example, when the microporous film is a layer with a multilayer construction. Heating with the laser can be adjusted to a location of the microporous film with the multilayer construction (e.g., multilayer film). The heating can be made in a pattern by directing the radiation across the surface to expose an area of material, or the radiation can be directed across the surface of a suitable mask so that a patterned area is exposed to the radiation. The microporous film may be positioned outside of the focal plane of the laser to adjust the level of heating.

For some applications such as heat seal films, recording media, and oil-absorbing cosmetic sheets, it has been shown that changing the microporous structure in a region of a microporous film can change the opacity in that region. See, for example, GB 2323327, published Sep. 23, 1998, GB 2252838, published Aug. 19, 1992, and U.S. Pat. App. Pub. No. 2003/091618 (Seth et al.). However, in some of these cases, the change is provided in a random fashion, for example, by an impact during the use of the film that cannot provide a predetermined pattern or image. A change in the microporous structure by impact may also not be permanent. In other cases, the change is only provided along the edge of a film and therefore does not provide at least one see-through region within an opaque, microporous region.

In some embodiments, the microporous film having an opaque, microporous region and at least one see-through region of lower porosity within the opaque, microporous region is a mechanical fastener. In some embodiments, the mechanical fastening elements of the mechanical fastener are male fastening elements. In some of these embodiments, the male fastening elements comprise upstanding posts having bases attached to the microporous film. The microporous film and the upstanding posts are typically integral (that is, formed at the same time as a unit, unitary). The microporous film is typically in the form of a sheet or web that may have an essentially uniform thickness with the upstanding posts directly attached to the microporous film.

Upstanding posts on a film can be made, for example, by conventional extrusion through a die and cast molding techniques. In some embodiments, a thermoplastic composition containing the beta-nucleating agent, cavitating agent, or diluent is fed onto a continuously moving mold surface with cavities having the inverse shape of the upstanding posts. The thermoplastic composition can be passed between a nip formed by two rolls or a nip between a die face and roll surface, with at least one of the rolls having the cavities (i.e., at least one of the rolls is a tool roll). Pressure provided by the nip forces the composition into the cavities. In some embodiments, a vacuum can be used to evacuate the cavities for easier filling of the cavities. The nip has a gap that is typically large enough such that a coherent film is formed over the cavities. The mold surface and cavities can optionally be air or water cooled before stripping the integrally formed film and upstanding posts from the mold surface such as by a stripper roll.

Suitable tool rolls can be made, for example, by forming (e.g., by computer numerical control with drilling, photo etching, using galvanic printed sleeves, laser drilling, electron beam drilling, metal punching, direct machining, or lost wax processing) a series of holes having the inverse shape of the upstanding posts into the cylindrical face of a metal mold or sleeve. Other suitable tool rolls include those formed from a series of plates defining a plurality of post-forming cavities about its periphery such as those described, for example, in U.S. Pat. No. 4,775,310 (Fischer). Cavities may be formed in the plates by drilling or photo-resist technology, for example. Other suitable tool rolls may include wire-wrapped rolls, which are disclosed along with their method of manufacturing, for example, in U.S. Pat. No. 6,190,594 (Gorman et al.). Another example of a method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

The upstanding posts, which may be made, for example, by any of the methods described above, may have a shape that tapers, for example, from base portion attached to the film to a distal tip. The base portion may have a larger width dimension than the distal tip, which may facilitate the removal of the post from the mold surface in the methods described above.

The male fastening elements in the mechanical fastener disclosed herein may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J (e.g., as shown and described in U.S. Pat. No. 5,953,797 (Provost et al.). The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter.

In some embodiments, the distal tips of the upstanding posts that are formed according to any of the above methods are deformed to form caps with loop-engaging overhangs. A combination heat and pressure, sequentially or simultaneously, may be used to deform the distal tips of the posts to form caps. In some embodiments, deforming comprises contacting the distal tips with a heated surface. The heated surface may be a flat surface or a textured surface such as that disclosed in U.S. Pat. No. 6,708,378 (Parellada et al.) or U.S. Pat. No. 5,868,987 (Kampfer et al.). In some embodiments, wherein the film with upstanding posts is a web of indefinite length, the deforming comprises moving the web in a first direction through a nip having a heated surface member and an opposing surface member such that the heated surface member contacts the distal tips. In these embodiments, the heated surface may be, for example, a capping roll. In some embodiments, the surface used to contact the distal tips is not heated. In these embodiments, the deformation is carried out with pressure and without heating. In some embodiments, the heated surface may be a heated roll opposite a curved support surface forming a variable nip having a variable nip length as described, for example, in U.S. Pat. No. 6,368,097 (Miller et al.). The curved support surface may curve in the direction of the heated roll, and the heated roll may include a feeding mechanism for feeding the film with upstanding posts through the variable nip to compressively engage the web between the heated roll and the support surface.

Another suitable method for forming a film with upstanding posts attached to the backing is profile extrusion, which is described, for example, in U.S. Pat. No. 4,894,060 (Nestegard). In this method a flow stream of a thermoplastic composition containing the beta-nucleating agent, cavitating agent, or diluent is passed through a patterned die lip (e.g., cut by electron discharge machining) to form a web having downweb ridges. The ridges are then transversely sliced at spaced locations along the extension of the ridges to form upstanding posts with a small separation caused by the cutting blade. It should be understood that "upstanding posts" do not include such ridges before they are cut. However, the patterned die lip may be considered a tool to provide a film having upstanding posts on a backing. The separation between the upstanding posts is then increased by stretching the film in the direction of the ridges using one of the stretching methods described above. The ridges themselves would also not be considered "loop-engaging" because they would not be able to engage loops before they are cut and stretched. In some embodiments, methods according to the present disclosure do not include cutting ribs (e.g., made by profile extrusion).

In addition to the continuous methods described above, it is also envisioned that films with upstanding posts can be prepared using batch processes (e.g., single piece injection molding). The film may have any suitable dimension, but length (L) and width (W) dimensions of at least 10 cm may be useful.

The upstanding posts, in any of the embodiments of the mechanical fastener including male fastening elements disclosed herein, which may be made, for example, by any of the methods described above, may have a variety of cross-sectional shapes. For example, the cross-sectional shape of the post may be a polygon (e.g., square, rectangle, hexagon, or pentagon), which may be a regular polygon or not, or the cross-sectional shape of the post may be curved (e.g., round or elliptical).

In some embodiments, the upstanding posts have a maximum height (above the film) of up to 3 millimeters (mm), 1.5 mm, 1 mm, or 0.5 mm and, in some embodiments, a minimum height of at least 0.05 mm, 0.075 mm, 0.1 mm, or 0.2 mm. In some embodiments, the posts have aspect ratio (that is, a ratio of height over a width dimension) of at least about 2:1, 3:1, or 4:1. The aspect ratio may be, in some embodiments, up to 10:1. For posts with caps, the caps are typically larger in area than the cross-sectional area of the posts. A ratio of a width dimension of the cap to the post measured just below the cap is typically at least 1.5:1 or 3:1 and may be up to 5:1 or greater. The capped posts are typically shorter than the posts before capping. In some embodiments, the capped posts have a height (above the film) of at least 0.025 mm, 0.05 mm, or 0.1 mm and, in some embodiments, up to 2 mm, 1.5 mm, 1 mm, or 0.5 mm. The posts, which may be capped or not, may have a cross-section with a maximum width dimension of up to 1 (in some embodiments, up to 0.75, 0.5, or 0.45) mm. In some embodiments, the posts have a cross-section with a width dimension between 10 μm and 250 μm. The term "width dimension" should be understood to include the diameter of a post with a circular cross-section. When the post has more than one width dimension (e.g., in a rectangular or elliptical cross-section shaped post or a post that tapers as described above), the aspect ratio described herein is the height over the largest width dimension.

The upstanding posts are typically spaced apart on the backing. The term "spaced-apart" refers to posts that are formed to have a distance between them. The bases of "spaced-apart" posts, where they are attached to the film, do not touch each other before or after stretching the film when the film is in an unbent configuration. In the mechanical fastener according to and/or made according to the present disclosure, the spaced-apart upstanding posts have an initial density (i.e., before any stretching of the film) of at least 10 per square centimeter ($cm^2$) (63 per square inch $in^2$). For example, the initial density of the posts may be at least $100/cm^2$ ($635/in^2$), $248/cm^2$ ($1600/in^2$), $394/cm^2$ ($2500/in^2$), or $550/cm^2$ ($3500/in^2$). In some embodiments, the initial density of the posts may be up to $1575/cm^2$ ($10000/in^2$), up to about $1182/cm^2$ ($7500/in^2$), or up to about $787/cm^2$ ($5000/in^2$). Initial densities in a range from $10/cm^2$ ($63/in^2$) to $1575/cm^2$ ($10000/in^2$) or $100/cm^2$ ($635/in^2$) to $1182/cm^2$ ($7500/in^2$) may be useful, for example. The spacing of the upstanding posts need not be uniform. After stretching the density of the upstanding posts is less than the initial density of the upstanding posts. In some embodiments, the upstanding posts have a density after stretching of at least 2 per square centimeter ($cm^2$) (13 per square inch $in^2$). For example, the density of the posts after stretching may be at least $62/cm^2$ ($400/in^2$), $124/cm^2$ ($800/in^2$), $248/cm^2$ ($1600/in^2$), or $394/cm^2$ ($2500/in^2$). In some embodiments, the density of the posts after stretching may be up to about $1182/cm^2$ ($7500/in^2$) or up to about $787/cm^2$ ($5000/in^2$). Densities after stretching in a range from $2/cm^2$ ($13/in^2$) to $1182/cm^2$ ($7500/in^2$) or $124/cm^2$ ($800/in^2$) to $787/cm^2$ ($5000/in^2$) may be useful, for example. Again, the spacing of the posts need not be uniform.

In some embodiments of the method of making a mechanical fastener according to the present disclosure, a melt of a polyolefin and a beta-nucleating agent is extruded to provide a film. The method includes cooling at least a portion of the melt to a temperature sufficient to form beta-spherulites (e.g., a temperature in a range from 60° C. to 120° C. or 90° C. to 120° C.) and forming upstanding posts on the film. In some of these embodiments, forming the upstanding posts on the film is carried out after cooling at least a portion of the melt (e.g., by exposing a solid film to a tool and heating). In other embodiments, a melt of a polyolefin and a beta-nucleating agent is extruded in the presence of a tool to provide the film having upstanding posts for at least a portion of the film. The film is then cooled to a temperature sufficient to form beta-spherulites. For example, the mold surface can be cooled to a temperature in a range from 60° C. to 120° C. or 90° C. to 120° C.

While unstructured films comprising polypropylene with beta-spherulites have been demonstrated to become microporous and increase in opacity upon stretching, high stretch ratios are reported to be required to achieve a desirable level of porosity or opacity. In some cases, stretch ratios exceeding 5:1, 10:1, or 20:1 are reported. See, e.g., U.S. Pat. No. 6,815,048 (Davidson et al.), U.S. Pat. Appl. Pub. No. 2006/0177632 (Jacoby), and UK Pat. App. GB 2323325, published Sep. 23, 1998. Typically the films are biaxially stretched. Unexpectedly, a film including upstanding posts comprising a semi-crystalline polyolefin and a beta-nucleating agent can be stretched at relatively low stretch ratios, and in some cases, in only one direction, to achieve high levels of porosity and opacity. Also, levels of porosity and opacity in stretched films having upstanding posts have been found to increase as the stretch temperature decreases. In some embodiments, the temperature range is from 50° C. to 110° C., 50° C. to 90° C., or 50° C. to 80°

C. In some embodiments, stretching at lower temperatures may be possible, for example, in a range from 25° C. to 50° C. It has unexpectedly been found that stretching the films having upstanding posts can be carried out at lower temperatures than flat films including a beta-nucleating agent previously described. For example, structured films of a semi-crystalline polyolefin containing a beta-nucleating agent can even be stretched at a temperature of up to 70° C. (e.g., in a range from 50° C. to 70° C. or 60° C. to 70° C.). Further details can be found in U.S. Pat. App. Pub. No. 2013/0149488 (Chandrasekaran et al.).

As described in the co-pending application, the upstanding posts are typically not affected by the stretching or are affected to a much lesser extent than the film and therefore retain beta-crystalline structure and are less microporous. The resulting stretched films can have several unique properties. For example, the micropores formed in the film along with stress-whitening can provide an opaque, white film while the upstanding posts are transparent. The visible contrast between the film and the upstanding posts may be enhanced by the presence of a colorant. Colorants may be added to a polyolefin before film formation, for example, using a color concentrate as described above. The colored films also undergo stress-whitening and microvoiding upon stretching, and these changes are manifested typically as a visible reduction in intensity of the color of the film. As a result, the stretched film may be a pastel color while the intensity of the color of the upstanding posts is maintained. If a low enough concentration of the color concentrate, for example, is used, the resulting stretched film may have an appearance of an almost white film with colored upstanding posts. Despite the fact that the upstanding posts are less microporous and more transparent, it should be understood that in the mechanical fastener disclosed herein, the film itself has an opaque, microporous region and at least one see-through region of lower porosity within the opaque, microporous region. The microporous film has a thickness that does not include the upstanding posts, and the at least one see-through region extends through the thickness of the microporous film.

In some embodiments of the mechanical fastener according to the present disclosure, the mechanical fastening elements are female fastening elements, for example, loops disposed on the microporous film having an opaque, microporous region and at least one see-through region of lower porosity within the opaque, microporous region. The loops may be part of a fibrous structure formed by any of several methods such as weaving, knitting, warp knitting, weft insertion knitting, circular knitting, or methods for making nonwoven structures. In some embodiments, the loops are included in a nonwoven web or a knitted web. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. Useful loop materials may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Referring again to FIG. 1, examples of loop tapes that may suitably be applied to the target area 68 to provide an exposed fibrous material 72, are disclosed, for example, in U.S. Pat. No. 5,389,416 (Mody et al.) and U.S. Pat. No. 5,256,231 (Gorman et al.) and EP 0,341,993 (Gorman et al.). As described in U.S. Pat. No. 5,256,231 (Gorman et al.), the fibrous layer in a loop material according to some embodiments can comprise arcuate portions projecting in the same direction from spaced anchor portions on a film. Any of the fibrous loop materials may be extrusion-bonded, adhesive-bonded, and/or sonically-bonded to the microporous film. For loop materials extrusion bonded to the microporous film, stretching the film to provide or enhance porosity is typically carried out after the extrusion bonding. Stretching the microporous film may be carried out before or after adhesively or sonically bonding the fibrous loop material to the microporous film.

In some embodiments, of mechanical fasteners according to the present disclosure, the microporous film is a substrate (e.g., tape backing) onto which a strip or patch having the mechanical fastening elements is attached. The strip or patch can include male or female fastening elements, and the substrate can be a tape backing of a fastening tape. In some embodiments, the mechanical fastener comprises female fastening elements in a fibrous layer. The fibrous layer may be bonded to a backing layer that is see-through and not microporous, and the microporous film having at least one see-through region within the opaque microporous region may be laminated to the side of the backing opposite the fibrous layer. The mechanical fastener may be such as that described in U.S. Pat. No. 5,256,231 (Gorman et al.). It is possible in these embodiments to see through the mechanical fastener to the microporous layer below. In some of these embodiments, the microporous film can be a first layer of multilayer construction comprising the first layer and a second layer, and a portion of the second layer, which may be colored or metalized, is visible through the at least one see-through region of lower porosity. In some of these embodiments, the microporous film can be included in a blown film sandwich of a colored film between two microporous films, at least one of which has at least one see-through region of lower porosity within the opaque, microporous region.

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are widely used in personal hygiene articles (that is, wearable disposable absorbent articles) to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. However, mechanical fasteners are useful for providing releasable attachment in numerous applications (e.g., abrasive discs, assembly of automobile parts, as well as personal hygiene articles).

The microporous regions in the fastening tapes or components thereof, including mechanical fasteners, according to the present disclosure provide advantages other than the contrast between the microporous region and the at least one see-through region. The ability of the microporous films to block the transmission of light (e.g., by scattering) allows them to be detected in inspection systems that rely upon shining a light onto a substrate and detecting the amount of light received from the area of the irradiated substrate. For example, in the manufacture of a personal hygiene article, the presence or position of a microporous film disclosed herein or a portion thereof incorporated into the article can be detected because of its ability to block ultraviolet, visible, and/or infrared light. The response of the microporous film to irradiation by at least one of ultraviolet, visible, or infrared light is evaluated. Subsequently, during manufacturing a personal hygiene article can be irradiated, and at least one of the ultraviolet, visible, or infrared radiation received from the irradiated personal hygiene article can be detected and analyzed for the predefined response of the microporous film. The position of the microporous film can be determined using an image analyzer that can detect predefined variations in grayscale values, for example, that correspond to the positions of the microporous film and other components. The ability of the microporous film disclosed herein to scatter infrared light allows it to be detected even when it is between other layers of materials in the composite article. For more information regarding methods of detecting microporous films in a composite article, see U.S. Pat. App. Pub. No. 2013/0147076 (Chandrasekaran et al.).

Furthermore, microporous films tend to have lower densities than their non-microporous counterparts. A low-density microporous film feels softer to the touch than films having comparable thicknesses but higher densities. The density of the film can be measured using conventional methods, for example, using helium in a pycnometer. In some embodiments, stretching a film containing beta-spherulites provides a decrease in density of at least three percent. In some embodiments, this stretching provides at decrease in density of at least 5 or 7.5 percent. For example, the stretching provides at decrease in density in a range from 3 to 15 percent or 5 to 10 percent. A percentage change in density that results from stretching the film is calculated by [(density before stretching−density after stretching)/density before stretching] times 100. The softness of the film can be measured, for example, using Gurley stiffness.

As described above in connection with FIG. 2, the microporous film may be a first layer of a laminate comprising the first layer and a second layer, and a portion of the second layer is visible through the at least one see-through region of lower porosity. It could be especially useful when the layer is colored. It is also possible for the microporous film useful for practicing the present disclosure to be a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A similar process that also includes co-extruding a continuous outer skin layer on one or both outer faces of the side-by-side co-extruded film as described in U.S. Pat. No. 6,669,887 (Hilston et al.) may also be useful. Management of the flow of different polymer compositions into side-by-side lanes can also be carried out using a single manifold die with a distribution plate in contrast to approaches that require multiple dies to achieve side-by-side co-extrusion. Further details about the die and the distribution plate can be found, for example, in U.S. Pat. Appl. Pub. No. 2012/0308755 (Gorman et al.). Side-by-side co-extruded films can also be made by other extrusion dies that comprise a plurality of shims and have two cavities for molten polymer, such as those dies described, for example, in Int. Pat. App. Pub. No. WO 2011/119323 (Ausen et al.) and U.S. Pat. App. Pub. No. 2014/0093716 (Hanschen et al.).

In some embodiments, the microporous film useful for practicing the present disclosure is a coextruded film having side-by-side first and second lanes, wherein the first lanes comprise the opaque, microporous region and at least one see-through region of lower porosity within the opaque, microporous region, and wherein the second lanes comprise a different polymer composition, which may not be microporous. In some embodiments, the microporous film is a multilayer film having first and second layers, wherein the first layer comprises the opaque, microporous region and at least one see-through region of lower porosity within the opaque, microporous region, and wherein the second layer comprises a different polymer composition, which may not be microporous. Suitable thermoplastic materials for the different polymer composition include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. In some embodiments, the different polymer composition (e.g., in the second lanes or second layer) includes an alpha nucleating agent (e.g., in polypropylene). In some embodiments, the different polymer composition includes a colorant such as a pigment or dye.

In some embodiments, the different polymer composition (e.g., in the second lanes or second layer) includes an elastomeric material. The term "elastomeric" refers to polymers from which films (0.002 to 0.5 mm thick) can be made that exhibit recovery from stretching or deformation. Exemplary elastomeric polymeric compositions which can be used in the segmented multicomponent polymeric films disclosed herein include thermoplastic elastomers such as ABA block copolymers, polyurethane elastomers, polyolefin elastomers (e.g., metallocene polyolefin elastomers), polyamide elastomers, ethylene vinyl acetate elastomers, and polyester elastomers. An ABA block copolymer elastomer generally is one where the A blocks are polystyrenic, and the B blocks are conjugated dienes (e.g., lower alkylene dienes). The A block is generally formed predominantly of substituted (e.g, alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, for example, in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastomers can be blended with block copolymer elastomers provided that the elastomeric properties are not adversely affected. Many types of thermoplastic elastomers are commercially available, including those from BASF under the trade designation "STYROFLEX", from Shell Chemicals under the trade designation "KRATON", from Dow Chemical under the trade designation "PEL-LETHANE" or "ENGAGE", from DSM under the trade designation "ARNITEL", from DuPont under the trade designation "HYTREL", and more. The thermoplastic elastomers including tetrablock styrene/ethylene-propylene/styrene/ethylene-propylene described in U.S. Pat. No. 6,669,887 (Hilston et al.) may also be useful.

For any of the embodiments of the fastening tape and mechanical fastener according to and/or made according to the present disclosure, the fastening tape or mechanical fastener may be in the form of a roll, from which smaller pieces (for example, mechanical fastener patches and fastening tape tabs) may be cut in a size appropriate to the desired application. In this application, the fastening tape and mechanical fastener may also be a fastening tape tab or mechanical fastening patch, respectively, that has been cut to a desired size, and the method of making a fastening tape or mechanical fastener can include cutting the fastening tape or mechanical fastener to a desired size. In some embodiments of the mechanical fastener, the second surface of the mechanical fastener (i.e., the surface opposite the first surface from which the mechanical fastening elements project) may be coated with an adhesive (e.g., a pressure sensitive adhesive). In such embodiments, when the mechanical fastener is in the form of a roll, a release liner may be applied to the exposed adhesive.

In some of these embodiments, the fastening tab or patch that has been cut from the fastening tape or mechanical fastener as described above can be incorporated into personal hygiene article. The fastening tape tab can be attached to a personal hygiene article, for example, by thermal lamination, adhesives (e.g., pressure sensitive adhesives), or other bonding methods (e.g., ultrasonic bonding, compression bonding, or surface bonding).

In some embodiments of the method of making a mechanical fastener disclosed herein, the method further comprises joining a second surface of the mechanical fastener (i.e., the surface opposite the first surface from which the mechanical fastening elements project) to a carrier. The mechanical fastener may be joined to a carrier by lamination (e.g., extrusion lamination), adhesives (e.g., pressure sensitive adhesives), or other bonding methods (e.g., ultrasonic bonding, compression bonding, or surface bonding). In some embodiments, the mechanical fastener may be joined to a carrier during the formation of the film with upstanding posts, and stretching to induce or enhance microporosity can be carried out after the mechanical fastener is joined to a carrier. The resulting article may be a fastening laminate, for example, a fastening tape tab joined to the backsheet of a personal hygiene article useful for joining the front waist region and the rear waist region.

In embodiments in which the release tape or mechanical fastener comprises the microporous film having the opaque, microporous region and at least one see-through region of lower porosity within the opaque, microporous region, the tape backing of the fastening tape or carrier for the mechanical fastener need not comprise the microporous film but may comprise a variety of suitable materials. For example, the tape backing or carrier may comprise woven webs, nonwoven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the tape backing or carrier is a fibrous material (e.g., a woven, nonwoven, or knit material). In some embodiments, the tape backing or carrier comprises multiple layers of nonwoven materials with, for example, at least one layer of a meltblown nonwoven and at least one layer of a spunbonded nonwoven, or any other suitable combination of nonwoven materials. For example, the tape backing or carrier may be a spunbond-meltbond-spunbond, spunbond-spunbond, or spunbond-spunbond-spunbond multilayer material. Or, the tape backing or carrier may be a composite web comprising any combination of nonwoven layers and dense film layers. The tape backing or carrier may be continuous (i.e., without any through-penetrating holes) or discontinuous (e.g. comprising through-penetrating perforations or pores) and may be colored.

Fibrous materials that provide useful tape backings or carriers for mechanical fasteners may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful tape backings or carriers may have any suitable basis weight or thickness that is desired for a particular application. For a fibrous tape backing or carrier, the basis weight may range, e.g., from at least about 20, 30, or 40 grams per square meter, up to about 400, 200, or 100 grams per square meter. The tape backing or carrier may be up to about 5 mm, about 2 mm, or about 1 mm in thickness and/or at least about 0.1, about 0.2, or about 0.5 mm in thickness.

One or more zones of the tape backing or carrier may comprise one or more elastically extensible materials extending in at least one direction when a force is applied and returning to approximately their original dimension after the force is removed. The term "elastic" refers to any material that exhibits recovery from stretching or deformation. Likewise, "nonelastic" materials, which do not exhibit recovery from stretching or deformation, may be useful for the tape backing or carrier as well.

In some embodiments where the tape backing or carrier is a fibrous web, joining thermoplastic components such as the microporous film to a tape backing or carrier comprises impinging heated gaseous fluid (e.g., ambient air, dehumidified air, nitrogen, an inert gas, or other gas mixture) onto a first surface of the fibrous web while it is moving; impinging heated fluid onto a surface of the microporous film while the continuous web is moving, wherein in some embodiments, the surface of the microporous film is the second surface opposite the first surface having mechanical fastening elements; and contacting the first surface of the fibrous web with the surface of the microporous film so that the first surface of the fibrous web is melt-bonded (e.g., surface-bonded or bonded with a loft-retaining bond) to the microporous film. Impinging heated gaseous fluid onto the first surface of the fibrous web and impinging heated gaseous fluid on the microporous film may be carried out sequentially or simultaneously. The term "surface-bonded" when referring to the bonding of fibrous materials means that parts of fiber surfaces of at least portions of fibers are melt-bonded to the surface of the microporous film in such a manner as to substantially preserve the original (pre-bonded) shape of the surface of the microporous film, and to substantially preserve at least some portions of the surface of the microporous film in an exposed condition, in the surface-bonded area. Quantitatively, surface-bonded fibers may be distinguished from embedded fibers in that at least about 65% of the surface area of the surface-bonded fiber is visible above the surface of the microporous film in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material before, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the surface of the microporous film bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the surface of the microporous film bonded thereto. The hot air should be limited so that it does not form a see-through region in the bonding area unless it is desired. Methods and apparatus for joining a continuous web to a fibrous carrier web using heated gaseous fluid may be found in U.S. Pat. Appl. Pub. Nos. 2011-0151171 (Biegler et al.) and 2011-0147475 (Biegler et al.).

Some Embodiments of the Disclosure

In a first embodiment, the present disclosure provides a fastening tape comprising:
 a tape backing comprising a fastening portion;
 an adhesive disposed on the fastening portion; and
 a release surface for the adhesive, wherein the release surface is a release tape attached along one of its edges to the tape backing or a release coating disposed on at least a portion of a surface of the tape backing;
 wherein at least one of the tape backing or the release surface comprises a microporous film having an opaque, microporous region and at least one see-through region of lower porosity within the opaque, microporous region.

In a second embodiment, the present disclosure provides the fastening tape of the first embodiment, wherein the tape backing comprises the microporous film having the opaque, microporous region and the at least one see-through region of lower porosity within the opaque, microporous region.

In a third embodiment, the present disclosure provides the fastening tape of the second embodiment, wherein the release surface is the release coating disposed on at least the portion of the surface of the tape backing.

In a fourth embodiment, the present disclosure provides the fastening tape of the first embodiment, wherein the release surface is the release tape comprising the microporous film having the opaque, microporous region and the at least one see-through region of lower porosity within the opaque, microporous region. The release tape may be attached along one of its edges to the tape backing by a separate strip attached to the tape backing and the release tape.

In a fifth embodiment, the present disclosure provides the fastening tape of any one of the first to fourth embodiments, further comprising a mechanical fastener attached to the adhesive on the fastening portion.

In a sixth embodiment, the present disclosure provides a personal hygiene article comprising a chassis with a topsheet, a backsheet, an absorbent component between the topsheet and the backsheet, first and second opposing longitudinal edges extending from a rear waist region to an opposing front waist region, and a fastening tab attached to the first longitudinal edge of the chassis in the rear waist region or the front waist region, wherein the fastening tab comprises a microporous film having an opaque, microporous region and at least one see-through region of lower porosity within the opaque, microporous region. The fastening tab may have any combination of the features of the first to fifth embodiments. The personal hygiene article can also be a pants style personal hygiene article including a chassis with a topsheet, a backsheet, an absorbent component between the topsheet and the backsheet, and the fastening tab attached to at least a portion of the backsheet. The fastening tape in this embodiment may be a disposal tape.

In a seventh embodiment, the present disclosure provides the personal hygiene article of the sixth embodiment, wherein the microporous film forms at least a portion of a tape backing of the fastening tab.

In an eighth embodiment, the present disclosure provides the personal hygiene article of the sixth or seventh embodiment, wherein the microporous film forms at least a portion of a release tape on the fastening tab.

In a ninth embodiment, the present disclosure provides the personal hygiene article of any one of the sixth to eighth embodiments, wherein the microporous film forms at least a portion of a mechanical fastener on the fastening tab.

In a tenth embodiment, the present disclosure provides a personal hygiene article comprising a chassis with a topsheet, a backsheet, an absorbent component between the topsheet and the backsheet, and a disposal tape attached to the backsheet, wherein the disposal tape comprises a microporous film having an opaque, microporous region and at least one see-through region of lower porosity within the opaque, microporous region.

In an eleventh embodiment, the present disclosure provides a mechanical fastener comprising: a microporous film having a thickness, an opaque, microporous region, and at least one see-through region of lower porosity within the opaque, microporous region, wherein the at least one see-through region extends through the thickness of the microporous film; and mechanical fastening elements on at least one surface of the mechanical fastener.

In a twelfth embodiment, the present disclosure provides the mechanical fastener of the eleventh embodiment, wherein the mechanical fastening elements are male fastening elements comprising upstanding posts having bases attached to the microporous film.

In a thirteenth embodiment, the present disclosure provides the mechanical fastener of the twelfth embodiment, wherein the male fastening elements further comprise caps distal from the microporous film.

In a fourteenth embodiment, the present disclosure provides the mechanical fastener of the twelfth or thirteenth embodiments, wherein the microporous region has greater opacity than the upstanding posts.

In a fifteenth embodiment, the present disclosure provides the mechanical fastener of the eleventh embodiment, wherein the mechanical fastening elements are fibrous loops disposed on the microporous film.

In a sixteenth embodiment, the present disclosure provides the mechanical fastener of the fifteenth embodiment, wherein fibrous loops are formed from a knitted or nonwoven material.

In a seventeenth embodiment, the present disclosure provides the mechanical fastener of any one of the eleventh to sixteenth embodiments, wherein the microporous film is a substrate onto which a strip having the mechanical fastening elements is attached.

In an eighteenth embodiment, the present disclosure provides the fastening tape, personal hygiene article, or mechanical fastener of any one of the first to seventeenth embodiments, wherein the at least one see-through region of lower porosity is included in a pattern of see-through regions of lower porosity within the opaque, microporous region.

In a nineteenth embodiment, the present disclosure provides the fastening tape, personal hygiene article, or mechanical fastener of any one of the first to eighteenth embodiments, wherein the at least one see-through region of lower porosity is in the form of a number, picture, symbol, geometric shape, alphabetical letter, bar code, or a combination thereof.

In a twentieth embodiment, the present disclosure provides the fastening tape, personal hygiene article, or mechanical fastener of any one of the first to nineteenth embodiments, wherein the microporous film is a first layer of a multilayer construction comprising the first layer and a second layer, and wherein a portion of the second layer is visible through the at least one see-through region of lower porosity.

In a twenty-first embodiment, the present disclosure provides the fastening tape, personal hygiene article, or mechanical fastener of the twentieth embodiment, wherein the first layer and second layer have different colors or different shades of the same color.

In a twenty-second embodiment, the present disclosure provides the fastening tape, personal hygiene article, or mechanical fastener of any one of the first to twenty-first embodiments, wherein the microporous film comprises a beta-nucleating agent.

In a twenty-third embodiment, the present disclosure provides the fastening tape, personal hygiene article, or mechanical fastener of any one of the first to twenty-second embodiments, wherein the microporous film comprises at least one of a filler or a diluent.

In a twenty-fourth embodiment, the present disclosure provides the fastening tape, personal hygiene article, or mechanical fastener of any one of the first to twenty-third embodiments, wherein the microporous film comprises at least one of propylene homopolymer, a copolymer of propylene and other olefins, or a blend of a polypropylene homopolymer and a different polyolefin.

In a twenty-fifth embodiment, the present disclosure provides a method of making a mechanical fastener, the method comprising:
  providing a mechanical fastener comprising mechanical fastening elements on at least one surface of a microporous film; and
  collapsing some pores in the microporous film to form at least one see-through region of lower porosity within an opaque, microporous region of the microporous film.

In a twenty-sixth embodiment, the present disclosure provides the method of the twenty-fifth embodiment, wherein providing the mechanical fastener comprises:
  forming upstanding posts on a film comprising at least one of a beta-nucleating agent, a filler, or a diluent; and
  stretching the film to provide the microporous film.

In a twenty-seventh embodiment, the present disclosure provides the method of the twenty-fifth embodiment, wherein providing the mechanical fastener comprises:
  bonding a fibrous loop web to a film comprising at least one of a beta-nucleating agent, a filler, or a diluent; and
  stretching the film to provide the microporous film.

In a twenty-eighth embodiment, the present disclosure provides the method of the twenty-fifth embodiment, wherein providing the mechanical fastener comprises:
  melt blending a crystallizable polymer and a diluent to form a melt;
  extruding the melt onto a mold to form upstanding posts on a film; and
  cooling to a temperature at which the polymer crystallizes and phase separates from the diluent to provide the microporous film having upstanding posts on a surface.

In a twenty-ninth embodiment, the present disclosure provides the method of the twenty-fifth embodiment, wherein providing the mechanical fastener comprises:
  melt blending a crystallizable polymer and a diluent to form a melt;
  extrusion laminating the melt to a fibrous loop web; and
  cooling to a temperature at which the polymer crystallizes and phase separates from the diluent to provide the microporous film having loops on at least one surface.

In a thirtieth embodiment, the present disclosure provides a method of making a fastening tape, the method comprising:
  providing a microporous film;
  collapsing some pores in the microporous film to form at least one see-through region of lower porosity within an opaque, microporous region of the microporous film;
  assembling at least a portion of the microporous film including the at least one see-through region of lower porosity and the opaque, microporous region into the fastening tape having a tape backing comprising a fastening portion and a release surface, wherein the release surface is a release tape attached along one of its edges to the tape backing or a release coating disposed on at least a portion of a surface of the tape backing; and
  coating an adhesive on the fastening portion;
  wherein at least one of the tape backing or the release surface comprises the microporous film having the opaque, microporous region and the at least one see-through region of lower porosity within the opaque, microporous region.

In a thirty-first embodiment, the present disclosure provides the method of the thirtieth embodiment, wherein providing the microporous film comprises stretching a film comprising at least one of a beta-nucleating agent, a filler, or a diluent.

In a thirty-second embodiment, the present disclosure provides the method of the thirtieth embodiment, wherein providing the microporous film comprises melt blending a crystallizable polymer and a diluent and cooling to a temperature at which the polymer crystallizes and phase separates from the diluent.

In a thirty-third embodiment, the present disclosure provides the method of the any one of the twenty-fifth to thirty-second embodiments, wherein collapsing some pores in the microporous film comprises heating the microporous film to collapse the pores to form the at least one see-through region of lower porosity.

In a thirty-fourth embodiment, the present disclosure provides the method of the thirty-third embodiment, wherein heating the microporous film is carried out with a heated, patterned roller.

In a thirty-fifth embodiment, the present disclosure provides the method of the thirty-third embodiment, wherein heating the microporous film is carried out with hot air.

In a thirty-sixth embodiment, the present disclosure provides the method of the thirty-third embodiment, wherein heating the microporous film is carried out with a laser.

In a thirty-seventh embodiment, the present disclosure provides the method of the thirty-sixth embodiment, wherein the microporous film is a layer in a multilayer construction, and wherein the heating with the laser is adjusted to a location of the microporous film within the multilayer construction.

In a thirty-eighth embodiment, the present disclosure provides the method of any one of the twenty-fifth to thirty-seventh embodiments, further comprising incorporating a portion of the fastening tape or the mechanical fastener into a personal hygiene article.

In a thirty-ninth embodiment, the present disclosure provides a method of making a personal hygiene article, the method comprising:
  providing a chassis with a topsheet, a backsheet, an absorbent component between the topsheet and the backsheet, and first and second opposing longitudinal edges extending from a rear waist region to an opposing front waist region;
  obtaining a fastening tab by cutting the fastening tape made according to the method of any one of the thirtieth to thirty-seventh embodiments; and
  attaching the fastening tab to the first longitudinal edge of the chassis in the rear waist region or the front waist region.

In a fortieth embodiment, the present disclosure provides a method of making a personal hygiene article, the method comprising:
  providing a chassis with a topsheet, a backsheet, an absorbent component between the topsheet and the backsheet, and first and second opposing longitudinal edges extending from a rear waist region to an opposing front waist region;
  obtaining a mechanical fastener by cutting the microporous film made according to the method of any one of the twenty-fifth to thirty-seventh embodiments; and
  attaching the mechanical fastener to the chassis in the rear waist region or the front waist region.

In order that this disclosure can be more fully understood, the following examples are set forth. It should be understood that these examples are for illustrative purposes only and are not to be construed as limiting this disclosure in any manner.

EXAMPLES

Example 1

A film with upstanding posts was prepared by feeding a stream of a polypropylene impact copolymer, obtained from the Dow Chemical Company, Midland, Mich., under the trade designation "DOW C700-35N POLYPROPYLENE RESIN" (98 weight %) and a beta nucleating master batch obtained from the Mayzo Corporation, Alpharetta, Ga., under the trade designation "MPM 1114" (2 weight %) through a 2 inch (5.08 cm) single screw extruder. The polymer density was reported by the manufacturer to be 0.902 g/cc as measured according to ASTM D972, and the melt flow index (MFI) was reported to be 35 (at 230° C. and under the load of 2.16 kg) as measured according to ASTM D1238. The beta nucleating master batch was pelletized and contained a high performance beta nucleant formulation dispersed in a polypropylene homopolymer resin. Seven barrel zones in the extruder were set at 176° C., 170° C., 180° C., 190° C., 200° C., 218° C., and 218° C., respectively. The molten resin was then fed through a sheet die to a rotating cylindrical mold. The temperature of the die was set at 218° C. and the temperature of cylindrical mold was set at 90° C. The screw speed was set at 80 rpm. The mold was water-cooled to provide rapid quenching that maintained the orientation in the polymer. The post density was 5200 posts per square inch (806 posts per square centimeter) arranged in a staggered array and the post shape was conical. The cross-sectional shape of the post at the base was circular with a diameter of 350 micrometers. The line speed was set such that the film thickness was 100 micrometers. The web was fed into a cap forming apparatus after slitting it to the width to fit the apparatus. The posts were capped with oval shaped caps using the procedure described in U.S. Pat. No. 5,845,375 (Miller et al.). The caps were subsequently deformed using the procedure described in U.S. Pat. No. 6,132,660 (Kampfer) to provide "hook heads with downwardly projecting fiber engaging portions". The film was then stretched in the machine direction by passing the web through two sets of rolls in which one roll was rotating faster that the other one. For each set of rolls, the bottom roll was a chrome roll, and the top roll was a rubber roll. For stretching, the temperature of each bottom chrome roll was set at 71° C. (160° F.) and that of each top rubber roll was set at 71° C. (160° F.). The draw ratio was 2:1 in the machine direction.

A 20 cm by 6 cm piece was cut from the film, and the sample was placed on a machined aluminum plate coated with 0.5 cm thick silicone rubber. The edges of the sample were fixed to the aluminum plate using adhesive tape. An aluminum plate that was engraved with a wave pattern was mounted to the top plate of a compression press which is movable by using compressed air. The top plate was heated to a surface temperature of 130° C. (266° F.). The sample was fixed to the bottom plate of the press, which is a fixed plate. The top plate was pressed against the bottom plate for 6 seconds in order to emboss the wave pattern on to the sample.

A 3.7 cm by 2.5 cm patch of the sample was adhesively bonded to a fastening tab. A photograph of the resulting fastening tab is shown in FIG. 3. Although not shown in FIG. 3, the nonwoven behind the sample was colored blue, and the blue was clearly visible behind the see-through regions 34 formed in the press.

Example 2

Example 2 was prepared from a film extruded, molded with posts that were subsequently capped, and stretched in the machine direction according to the method of Example 1. A 20 cm by 6 cm sample of the stretched film was cut from the film. The sample was exposed to laser radiation at 10.6 micron wavelength from a $CO_2$ laser, E-400 from Coherent, Inc., Santa Clara, Calif. The laser energy was directed across the sample by a scanner Model HPLK 1330 from GSI Group, Billerica, Mass. The sample was positioned at a distance of approximately 510 mm from the scanner housing (whereas the focal plane of the scanner system was located at approximately 560 mm from the scanner housing). In the plane of the sample, the spot size for the laser beam was determined to be approximately 0.9 mm in width with a nearly circular shape. To provide a patterned exposure, the laser beam was scanned in a raster motion to create a filled shape of the trademarked logo of 3M Company, St. Paul, Minn., roughly 1 cm in height. The laser beam with a power of approximately 25 Watts was scanned at a speed of approximately 930 mm/sec in a raster motion across the mask with successive lines separated by approximately 0.5 mm. The laser radiation was incident upon the sample material and affected the change in appearance.

Example 3

A formed sheet of 9 denier polypropylene fibers was prepared according to the method of Example Number 1 of U.S. Pat. No. 5,256,231 (Gorman et al.) Polypropylene obtained from the Dow Chemical Company under the trade designation "DOW C700-35N POLYPROPYLENE RESIN" (98 weight %) and the beta nucleating master batch obtained from the Mayzo Corporation under the trade designation "MPM 1114" (2 weight %) were extruded through a die at a die temperature of 420° F. (216° C.) and onto the anchor portions of the formed sheet of fibers just before the nip between the first corrugating roller and a cooling roller in an amount appropriate to form the thermoplastic backing layer and cause it to be about 0.0381 centimeter thick with the anchor portions of the formed sheet of fibers embedded therein, whereupon the formed sheet of fibers and the thermoplastic backing layer moved through the nip between the first corrugating roller and the cooling roller and about 200 degrees around the periphery of the cooling roller, which was at a temperature of about 85° C. to ensure adequate cooling of the thermoplastic backing layer. The laminate was then stretched in the machine direction by passing the web through two sets of rolls in which one roll was rotating faster that the other one. For each set of rolls, the bottom roll was a chrome roll, and the top roll was a rubber roll. For stretching, the temperature of each bottom chrome roll was set at 71° C. (160° F.) and that of each top rubber roll was set at 71° C. (160° F.). The draw ratio was 1.4:1 in the machine direction. The laminate was then passed through a heated nip consisting of one patterned roll at the bottom and a polished chrome roll on top. The pattern roll had the pattern shown in FIG. 2. The surface temperature of the patterned roll was set to 140° C. with a nip pressure of 1000 N. The nip gap was set to 0.005 cm. The laminate in the patterned areas was see-through so that colored sheets placed behind the laminate could easily be seen.

Example 4

The poly(vinylidene fluoride) (PVDF) polymer pellets obtained from Solvay Solexis, Thorofare, N.J., under trade name "SOLEF 1012" were introduced into the hopper of a 25 mm co-rotating twin-screw extruder with an approximate total extrusion rate of 3.6-4.5 kilograms per hour and a screw speed of 150 RPM. The nucleating agent CHROMOPHTAL Blue A3R (Ciba Specialty Chemicals, Hawthorne, N.Y.) in powder form, was premixed with the glyceryl triacetate diluent obtained from (Eastman Kodak Co., Rochester, N.Y.) in a Mini-Zeta bead mill and then fed, with additional diluent by a feeding device into the extruder via a port in the extruder wall intermediate the hopper and the extruder exit. The polymer to diluent ratio was varied slightly in accordance with the amount of nucleator used, but was generally approximately 0.41:1.0. The extruder had eight zones with a temperature profile of zone 1 at 204° C., zone 2 at 266° C., zone 3 at 266° C., zone 4 at 221° C., zone 5 at 182° C., zone 6 at 182° C., zone 7 at 182° C. The melt was subsequently pumped through a double-chromed coat-hanger slot film die, cast onto a chrome roll that ranged from 52° C. and then wound into a roll. Film samples were cut from the rolls and placed in metal frames measuring 15 cm by 28 cm. The frames were then placed in small pans of deionized water for 20 minutes (effectively removing the TRIACETIN diluent from the films) and then allowed to dry in ambient air. The washed film samples were then stretched biaxially 1.75 by 1.75 on a TM Long Film Stretcher (TM Long Co., Somerville, N.J.) at 132° C. The films were held in the stretcher for 2-5 minutes at 132° C. after stretching was complete to anneal the film. A 20 cm by 6 cm piece was cut from the film, and the sample was placed on a machined aluminum plate coated with 0.5 cm thick silicone rubber. The edges of the sample were fixed to the aluminum plate using adhesive tape. An aluminum plate that was engraved with a wave pattern was mounted to the top plate of a compression press which is movable by using compressed air. The top plate was heated to a surface temperature of 130° C. (266° F.). The sample was fixed to the bottom plate of the press, which is a fixed plate. The top plate was pressed against the bottom plate for 6 seconds in order to emboss the wave pattern on to the sample.

Example 5

A sheet of film was made as described in Example 1 with the exception that a smooth chrome roll was used instead of a rotating cylindrical mold, and no upstanding posts were formed on the film. The film was subsequently stretched as described in Example 1.

A sample of the film was exposed to laser radiation at 10.6 micron wavelength from a $CO_2$ laser, E-400 from Coherent, Inc., Santa Clara, Calif. The laser energy was directed across the sample by a scanner Model HPLK 1330 from GSI Group, Billerica, Mass. The sample was positioned at a distance of approximately 510 mm from the scanner housing (whereas the focal plane of the scanner system was located at approximately 560 mm from the scanner housing). In the plane of the sample, the spot size for the laser beam was determined to be approximately 0.9 mm in width with a nearly circular shape. To provide a patterned exposure, the laser beam was scanned in a raster motion to create a filled shape of a rectangle, dimensions 2.5 cm by 2 cm. Four of such rectangles were made. The laser beam with a power of approximately 25 Watts was scanned at a speed of approximately 930 mm/sec in a raster motion across the mask with successive lines separated by approximately 0.5 mm. The laser radiation was incident upon the sample material and affected the change in appearance. The square patterned film was then cut into a sheet 20 cm by 12 cm, and colored sheets were attached underneath with a double sided tape. The colored sheets could be readily seen through the rectangles.

This film may be useful, for example, as a tape backing for a fastening tape, disposal tape, or release tape.

Illustrative Example 1

A sample prepared from a film extruded, molded with posts that were subsequently capped, and stretched in the machine direction according to the method of Example 1, with the exception that the stretch ratio in the machine direction was 2:1, was analyzed by X-ray Diffraction to determine the relative levels of beta-crystals and alpha-crystals in the sample. A portion of each structured film was applied to an aluminum open-backed specimen holder using double-coated tape on the edges. Reflection geometry data were collected in the form of a survey scan by use of a Philips vertical diffractometer (PANalytical, Natick, Mass.), copper Kα radiation, and proportional detector registry of the scattered radiation. The diffractometer was fitted with variable incident beam slits, fixed diffracted beam slits, and graphite diffracted beam monochromator. The survey scan was conducted from 5 to 55 degrees (2θ) using a 0.04 degree step size and 6 second dwell time. X-ray generator settings of 45 kV and 35 mA were employed.

The identification of individual peak positions was accomplished by comparison to values reported in the reference by Turner Jones, J. M. Aizlewood, and D. R. Beckett (*Die Makromolekulare Chemie*, Vol 75, Issue 1 (1964) p 134).

The diffraction patterns were subjected to profile fitting to using the analysis software JADE version 9.0 (Materials Data, Inc., Livermore, Calif.) to evaluate alpha form (110), (040), and (130) maxima as well as the beta form (300) maximum. The level of beta form present was determined as a factor (K) using the following equation: $K=I(300)_\beta/[I(300)_\beta+I(110)_\alpha+I(040)_\alpha+I(130)_\alpha]$ The individual terms of the equation are define as follows: $I(300)_\beta$ is the intensity of beta form (300) maximum; $I(110)_\alpha$ is the intensity of alpha form (110) maximum; $I(040)_\alpha$ is the intensity of alpha form (040) maximum; and $I(130)_\alpha$ is the intensity of alpha form (130) maximum. The calculated K-value varies from 0, for a sample with no beta crystals, to 1.0 for a sample with all beta-crystals. The K-value for the sample was 0.54.

Furthermore, thermal analysis of the sample was conducted at a heating rate of 10° C./min using a model Q-2000 differential scanning calorimeter (DSC) (TA instruments, New Castle, Del.) that was calibrated for temperature and enthalpy using an indium standard having a melting point of 165.5° C. The DSC scan was run under non-isothermal conditions. Approximately 10 mg of sample was used for the run. During the first thermal scan, the sample was heated at a scanning rate of 10° C./min to 200° C. and kept at this temperature isothermally for 1 minute, in order to erase the thermal history. The sample was subsequently cooled at 10° C./min to room temperature. The sample was reheated at a rate 10° C./min up to 200° C. and the second scan results were recorded and reported. The melting temperatures ($T_m$ in ° C.) and the heat of fusion data ($\Delta H_f$ in joules/gram) for both alpha and beta phases were recorded. The sample exhibited dual melting temperatures ($T_m$ (alpha) of 164.5° C. and $T_m$ (beta) of 150.2 (° C.) that were consistent with the presence of both alpha and beta crystal phases. The heats of fusion for the alpha and beta phases were 26.2 and 46.0, respectively.

Opacity of the sample was measured according to the ASTM E-284 using a LabScan XE spectrophotometer (Hunterlab, Reston, Va.). After standardizing the sensor of the instrument, the sample was placed under the specimen port against a black back up tile and the "L" value of color measurement was recorded. The "L" value is one of three standard parameters in the CIELAB color space scale established by the International Commission on Illumination. "L" is a brightness value, ranging from 0 (black) to 100 (highest intensity). This procedure was repeated with the sample placed against a white tile. For each step the sample was rotated 90 degrees and the average of the two readings was recorded. Opacity (reported in %) was calculated by the formula: % Opacity=$(L_{Black}/L_{White})*100$. The opacity of the sample was 91.4%.

Grayscale measurement of the sample was collected using an IMPACT A20 digital camera (PPT Vision, Bloomington, Minn.) equipped with a CMOS (complementary metal oxide semiconductor) image sensor and the IMPACT Software Suite. The one meter long samples in the machine direction (MD) were held under tension by hand between two rollers. The samples were illuminated from behind the film side (i.e. non-post side) with a 940 nm wavelength light source. The detection camera was mounted approximately five feet above the structured film samples with the post side facing the camera. The grayscale intensity measurements were taken in the transmission mode using a numeric scale ranging from 0 (high opacity) to 255 (low opacity). The grayscale intensity was recorded at three different MD sampling points. The mean value for the samples was 40.

Illustrative Example 2

A sample was prepared from a film extruded, molded with posts that were subsequently capped, and stretched in the machine direction according to the method of Example 1, with the exception that the stretch ratio in the machine direction was 2:1, and during the stretching, the roll temperatures were set at 60° C. The pore size (μm) in the microporous film was determined by measuring bubble point according to ASTM F-316-80. The largest effective pore size that was measured was 0.16 μm.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A mechanical fastener comprising:
   a microporous film having a thickness, an opaque, microporous region, and at least one see-through region of lower porosity within the opaque, microporous region, wherein the at least one see-through region of lower porosity extends through the thickness of the microporous film; and
   mechanical fastening elements on at least one surface of the mechanical fastener, wherein the mechanical fastening elements are male fastening elements comprising upstanding posts having bases directly attached to the microporous film, or wherein the mechanical fastening elements are fibrous loops directly bonded to the microporous film.

2. The mechanical fastener of claim 1, wherein the mechanical fastening elements are male fastening elements comprising upstanding posts having bases directly attached to the microporous film.

3. The mechanical fastener of claim 1, wherein the mechanical fastening elements are fibrous loops directly bonded to the microporous film.

4. The mechanical fastener of claim 1, wherein the at least one see-through region of lower porosity is included in a pattern of see-through, nonporous regions within the opaque, microporous region.

5. The mechanical fastener of claim 1, wherein the at least one see-through region of lower porosity is in the form of a number, symbol, picture, geometric shape, bar code, an alphabetical letter, or a combination thereof.

6. The mechanical fastener of claim 1, wherein the microporous film is a first layer of a multilayer construction comprising the first layer and a second layer, and wherein a portion of the second layer is visible through the at least one see-through region of lower porosity.

7. The mechanical fastener of claim 1, wherein the microporous film comprises a beta-nucleating agent.

8. A method of making the mechanical fastener of claim 1, the method comprising:
provoiding a mechanical fastener comprising mechanical fastening elements on at least one surface and a microporous film, wherein the mechanical fastening elements are male fastening elements comprising upstanding posts having bases directly attached to the microporous film, or wherein the mechanical fastening elements are fibrous loops directly bonded to the microporous film; and
collapsing some pores in the microporous film to form the at least one see-through region of lower porosity within an opaque, microporous region of the microporous film.

9. The method of claim 8, wherein collapsing some pores in the microporous film comprises heating the microporous film to collapse the pores to form the at least one see-through region of lower porosity.

10. The method of claim 8, further comprising incorporating the mechanical fastener into a personal hygiene article.

11. The mechanical fastener of claim 1, wherein the microporous film comprises at least one of propylene homopolymer, a copolymer of propylene and other olefins, or a blend of a polypropylene homopolymer and a different polyolefin.

12. The mechanical fastener of claim 2, wherein the at least one see-through region of lower porosity is included in a pattern of see-through, nonporous regions within the opaque, microporous region.

13. The mechanical fastener of claim 2, wherein the at least one see-through region of lower porosity is in the form of a number, symbol, picture, geometric shape, bar code, an alphabetical letter, or a combination thereof.

14. The mechanical fastener of claim 2, wherein the microporous film is a first layer of a multilayer construction comprising the first layer and a second layer, and wherein a portion of the second layer is visible through the at least one see-through region of lower porosity.

15. The mechanical fastener of claim 2, wherein the microporous film comprises a beta-nucleating agent.

16. The mechanical fastener of claim 14, wherein the first layer and second layer have different colors or different shades of the same color.

17. The mechanical fastener of claim 2, wherein the microporous film comprises at least one of propylene homopolymer, a copolymer of propylene and other olefins, or a blend of a polypropylene homopolymer and a different polyolefin.

18. The mechanical fastener of claim 2, wherein the male fastening elements further comprise caps distal from the microporous film.

19. The mechanical fastener of claim 2, wherein the microporous region has greater opacity than the upstanding posts.

20. The mechanical fastener of claim 6, wherein the first layer and second layer have different colors or different shades of the same color.

* * * * *